(12) United States Patent
Frank et al.

(10) Patent No.: US 6,309,832 B1
(45) Date of Patent: Oct. 30, 2001

(54) METHOD TO DETECT IGE

(75) Inventors: Glenn R. Frank, Wellington; James P. Porter, Fort Collins; Keith E. Rushlow, Fort Collins; Donald L. Wassom, Fort Collins, all of CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/285,873

(22) Filed: Mar. 31, 1999

Related U.S. Application Data

(62) Division of application No. 08/756,387, filed on Nov. 26, 1996, now Pat. No. 5,945,294.

(51) Int. Cl.[7] .......................... C12Q 1/58; G01N 33/53; G01N 33/567; G01N 33/569
(52) U.S. Cl. ................. 435/6; 435/7.1; 435/7.2; 435/7.21; 435/7.3; 435/7.31; 435/7.32; 435/7.5; 435/7.93; 435/7.94; 435/7.95
(58) Field of Search ................. 435/6, 7.1, 7.2, 435/7.21, 7.3, 7.31, 7.32, 7.5, 7.93, 7.94, 7.95

(56) References Cited

U.S. PATENT DOCUMENTS 4,962,035  10/1990  Leder et al. .................. 435/320

FOREIGN PATENT DOCUMENTS

| 5113443 | 5/1993 | (JP) . |
| WO 90/04640 | 5/1990 | (WO) . |
| WO 91/06570 | 5/1991 | (WO) . |

OTHER PUBLICATIONS

Kochan, et al., "Isolation of the Gene Coding for the Alpha Subunit of the Human High Affinity IgE Receptor," (1988) *Nucleic Acids Res. 16*(8), p. 3584.
Küster, et al., "Characterization and Expression of the Gene for the Human Fc Receptor γ Subunit,"(1990) *J. Biol. Chem. 265*(11), pp. 6448–6452.
Küster, et al., "The Gene and cDNA for the Human High Affinity Immunoglobulin E Receptor β Chain and Expression of the Complete Human Receptor," (1992) *J. Biol. Chem. 267*(18), pp. 12782–12787.
Lowenthal, et al., "Passive Transfer of IgE–Mediated Cutaneous Reactivity in Heterologous Species," (1993) *Annals of Allergy 71*, pp. 481–484.
Pang, et al., "Characterization of the Gene for the Human High Affinity IgE Receptor (FcεRI) α–Chain," (1993) *J. Immunol. 151*(11), pp. 6166–6174.
Shimizu, et al., "Human and Rat Mast Cell High–Affinity Immunoglubulin E Receptors: Characterization of Putative α–Chain Gene Products,"(1988), *Proc. Natl. Acad. Sci. USA* (85), pp. 1907–1911.
Patent Abstract of Japan, vol. 095, No. 007, Aug. 31, 1995 and JP 07 092167 A (Kinki Univ;; Others: 01), Apr. 7, 1995.
Patent Abstract of Japan, vol. 095, No. 006, Jul. 31, 1995 and JP 07 072150 A (Tonen Corp.; Others: 01), Mar. 7, 1995.

*Primary Examiner*—Rodney P. Swartz
(74) *Attorney, Agent, or Firm*—Heska Corporation

(57) ABSTRACT

The present invention includes a method to detect IgE using a human Fc epsilon receptor ($Fc_\epsilon R$) to detect IgE antibodies in a biological sample from a cat, a dog, or a horse. The present invention also relates to kits to perform such methods.

20 Claims, 11 Drawing Sheets

METHOD TO DETECT IGE

CROSS REFERENCE TO RELATED APPLICATIONS

This application is a divisional of U.S. application Ser. No. 08/756,387, filed Nov. 26, 1996, entitled "Method to detect IgE" now U.S. Pat. No. 5,945,294.

FIELD OF THE INVENTION

The present invention relates to a novel method to detect epsilon immunoglobulin (IgE). The present invention also includes novel kits to detect IgE as well as methods to produce the detection reagent.

BACKGROUND OF THE INVENTION

Diagnosis of disease and determination of treatment efficacy are important tools in medicine. In particular, detection of IgE production in an animal can be indicative of disease. Such diseases include, for example, allergy, atopic disease, hyper IgE syndrome, internal parasite infections and B cell neoplasia. In addition, detection of IgE production in an animal following a treatment is indicative of the efficacy of the treatment, such as when using treatments intended to disrupt IgE production.

Until the discovery of the present invention, detection of IgE in samples obtained from non-human animals has been hindered by the absence of suitable reagents for detection of IgE. Various compounds have been used to detect IgE in IgE-containing compositions. In particular, antibodies that bind selectively to epsilon idiotype antibodies (i.e., anti-IgE antibodies) have been used to detect IgE. These anti-IgE antibodies, however, can cross-react with other antibody idiotypes, such as gamma isotype antibodies. The discovery of the present invention includes the use of a Fc epsilon receptor ($Fc_\epsilon R$) molecule to detect the presence of IgE in a putative IgE-containing composition. A $Fc_\epsilon R$ molecule provides an advantage over, for example anti-IgE antibodies, to detect IgE because a $Fc_\epsilon R$ molecule can bind to an IgE with more specificity (i.e., less idiotype cross-reactivity) and more sensitivity (i.e., affinity) than anti-IgE binding antibodies.

Lowenthal et al., 1993, *Annals of Allergy* 71:481–484, dog serum can transfer cutaneous reactivity to a human. While it is possible that Lowenthal et al. properly teach the binding of human $Fc_\epsilon R$ to canine IgE. Lowenthal et al., however, do not provide data defining the particular cellular proteins responsible for the transfer of cutaneous reactivity. As such, a skilled artisan would conclude that the transfer of cutaneous reactivity taught by Lowenthal et al. could be due to a variety of different molecular interactions and that the conclusion drawn by Lowenthal et al. is merely an interpretation. In addition, Lowenthal et al. do not teach the use of purified human $Fc_\epsilon R$ to detect canine IgE. The subunits of human $Fc_\epsilon R$ have been known as early as 1988 and have never been used to detect canine, feline or equine IgE. Indeed, U.S. Pat. No. 4,962,035, to Leder et al., issued Oct. 9, 1990, discloses human $Fc_\epsilon R$ but does not disclose the use of such a human $Fc_\epsilon R$ to detect human or non-human IgE. The use of purified human $Fc_\epsilon R$ avoids complications presented by use of $Fc_\epsilon R$ bound to a cell, such as non-specific binding of the $Fc_\epsilon R$-bearing cell due to additional molecules present on the cell membrane. That purified human $Fc_\epsilon R$ detects non-human IgE is unexpected because inter-species binding between a $Fc_\epsilon R$ and an IgE is not predictable. For example, human $Fc_\epsilon R$ binds to rat IgE but rat $Fc_\epsilon R$ does not bind to human IgE.

The high affinity $Fc_\epsilon R$ consists of three protein chains, alpha, beta and gamma. Prior investigators have disclosed the nucleic acid sequence for: the alpha chain (Kochan et al., *Nucleic Acids Res.* 16:3584, 1988; Shimizu et al., *Proc. Natl. Acad. Sci. USA* 85:1907–1911, 1988; and Pang et al., *J. Immunol.* 151:6166–6174, 1993); the beta chain (Kuster et al., *J. Biol. Chem.* 267:12782–12787, 1992); and the gamma chain (Kuster et al., J. BioL Chem. 265:6448–6452, 1990).

Thus, methods and kits are needed in the art that will provide specific detection of non-human IgE.

SUMMARY OF THE INVENTION

The present invention includes detection methods and kits that detect IgE. One embodiment of the present invention is a method to detect IgE comprising: (a) contacting an isolated human $Fc_\epsilon$ receptor ($Fc_\epsilon R$) molecule with a putative IgE-containing composition under conditions suitable for formation of a $Fc_\epsilon R$ molecule:IgE complex, wherein the IgE is selected from the group consisting of canine IgE, feline IgE and equine IgE; and (b) determining the presence of IgE by detecting the $Fc_\epsilon R$ molecule:IgE complex, the presence of the $Fc_\epsilon R$ molecule:IgE complex indicating the presence of IgE. A preferred $Fc_\epsilon R$ molecule in which a carbohydrate group of the $Fc_\epsilon R$ molecule is conjugated to biotin.

Another embodiment of the present invention is a method to detect IgE comprising: (a) contacting a recombinant cell with a putative IgE-containing composition under conditions suitable for formation of a recombinant cell:IgE complex, in which the recombinant cell includes: a recombinant cell expressing a human $Fc_\epsilon R$ molecule; and a recombinant cell expressing an antibody that binds selectively to an IgE including canine IgE, feline IgE and equine IgE; and (b) determining the presence of IgE by detecting the recombinant cell:IgE complex, the presence of the recombinant cell:IgE complex indicating the presence of Ig. A preferred recombinant cell includes a RBL-h$Fc_\epsilon R$ cell.

Another embodiment of the present invention is a method to detect flea allergy dermatitis comprising: (a) immobilizing a flea allergen on a substrate; (b) contacting the flea allergen with a putative IgE-containing composition under conditions suitable for formation of an antigen:IgE complex bound to said substrate; (c) removing non-bound material from the substrate under conditions that retain antigen:IgE complex binding to the substrate; and (c) detecting the presence of the antigen:IgE complex by contacting the antigen:IgE complex with a $Fc_\epsilon R$ molecule. Preferably, the flea allergen is a flea saliva antigen and more preferably flea saliva products and/or flea saliva proteins.

The present invention also includes a kit for performing methods of the present invention. One embodiment is a kit for detecting IgE comprising a human $Fc_\epsilon$ receptor ($Fc_\epsilon R$) molecule and a means for detecting an IgE including canine IgE, feline IgE and equine IgE. Another embodiment is a general allergen kit comprising an allergen common to all regions of the United States and a human $Fc_\epsilon$ receptor ($Fc_\epsilon R$) molecule. Another embodiment is a kit for detecting flea allergy dermatitis comprising a human $Fc_\epsilon$ receptor ($Fc_\epsilon R$) molecule and a flea allergen.

Another embodiment of the present invention is an isolated human $Fc_\epsilon$ receptor ($Fc_\epsilon R$) alpha chain protein, in which a carbohydrate group of the $Fc_\epsilon R$ alpha chain protein is conjugated to biotin. A preferred $Fc_\epsilon R$ alpha chain protein comprises $PhFc_\epsilon R\alpha_{172}$—BIOT.

DETAILED DESCRIPTION OF THE INVENTION

Figure 1:
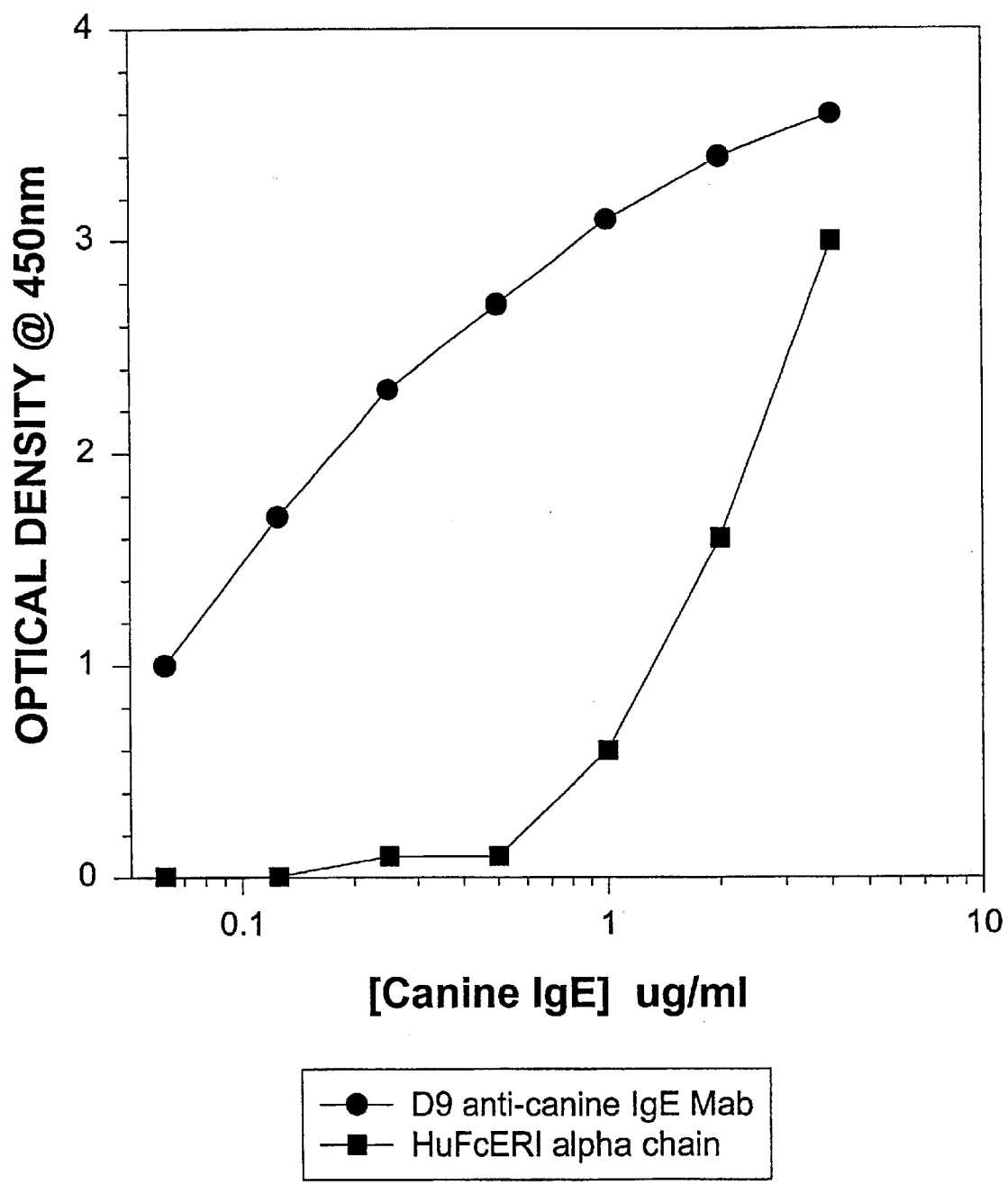
FIG. 1 depicts ELISA results using biotinylated alpha chain of human $Fc_\epsilon R$ to detect canine IgE antibodies.
Figure 2:
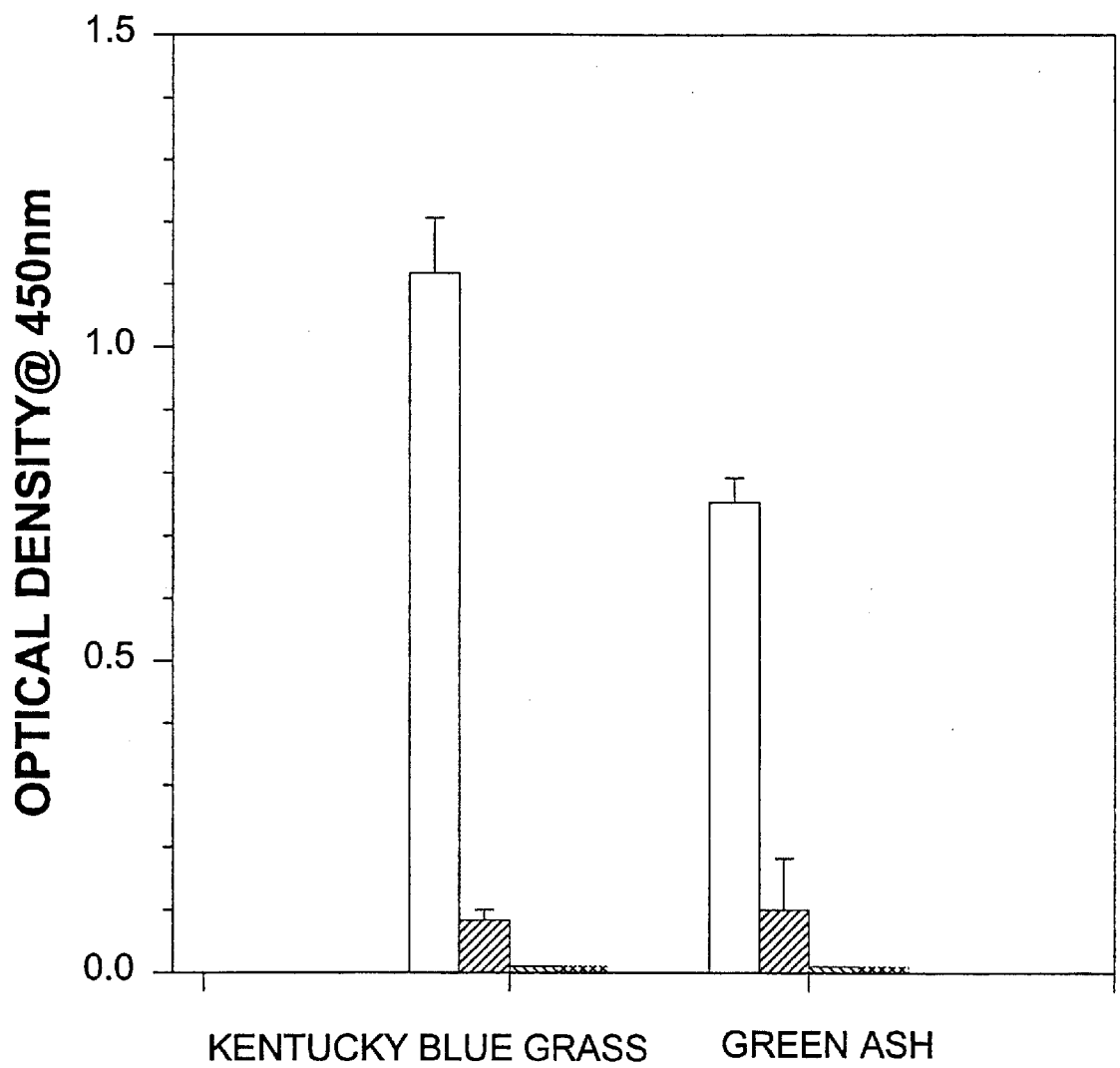
FIG. 2 depicts ELISA results using biotinylated alpha chain of human Fc$_\epsilon$R to detect plant allergen-specific canine IgE antibodies.

The present invention relates to the discovery that purified high affinity human Fc epsilon receptor (i.e., Fc$_\epsilon$RI; referred to herein as Fc$_\epsilon$R) can be used in certain non-human (i.e., canine, feline or equine) epsilon immunoglobulin (referred to herein as IgE or IgE antibody)-based detection (e.g., diagnostic, screening) methods and kits. The use of human Fc$_\epsilon$R to detect non-human IgE is unexpected because canine, feline and equine immune systems are different from the human immune system, as well as from each other (i.e., molecules important to the immune system usually are species specific).

One embodiment of the present invention is a method to detect a non-human IgE using an isolated human Fc$_\epsilon$R molecule. It is to be noted that the term "a" entity or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds.

According to the present invention, an isolated, or biologically pure, Fc$_\epsilon$R molecule, is a molecule that has been removed from its natural milieu. As such, "isolated" and "biologically pure" do not necessarily reflect the extent to which the molecule has been purified. An isolated human Fc$_\epsilon$R molecule of the present invention can be obtained from its natural source (e.g., from a human mast cell), can be produced using recombinant DNA technology or can be produced by chemical synthesis.

A Fc$_\epsilon$R molecule (also referred to herein as Fc$_\epsilon$R or Fc$_\epsilon$R protein) of the present invention can be a full-length protein, a portion of a full-length protein or any homolog of such a protein. As used herein, a protein can be a polypeptide or a peptide. A Fc$_\epsilon$R molecule of the present invention can comprise a complete Fc$_\epsilon$R (i.e., alpha, beta and gamma Fc$_\epsilon$R chains), an alpha Fc$_\epsilon$R chain (also referred to herein as Fc$_\epsilon$R α chain) or portions thereof. Preferably, a Fc$_\epsilon$R molecule comprises at least a portion of a Fc$_\epsilon$R α chain that binds to IgE, i.e., that is capable of forming an immunocomplex with an IgE constant region. Preferably, a Fc$_\epsilon$R molecule of the present invention binds to IgE with an affinity of about $K_A \approx 10^8$, more preferably with an affinity of about $K_A \approx 10^9$ and even more preferably with an affinity of about $K_A \approx 10^{10}$.

An isolated Fc$_\epsilon$R molecule of the present invention, including a homolog, can be identified in a straight-forward manner by the Fc$_\epsilon$R molecule's ability to form an immunocomplex with an IgE. Examples of Fc$_\epsilon$R homologs include Fc$_\epsilon$R proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of forming an immunocomplex with an IgE.

Fc$_\epsilon$R homologs can be the result of natural allelic variation or natural mutation. Fc$_\epsilon$R homologs of the present invention can also be produced using techniques known in the art including, but not limited to, direct modifications to the protein or modifications to the gene encoding the protein using, for example, classic or recombinant DNA techniques to effect random or targeted mutagenesis.

According to the present invention, a human Fc$_\epsilon$R α chain of the present invention is encoded by at least a portion of the nucleic acid sequence of the coding strand of a cDNA encoding a full-length Fc$_\epsilon$R α chain protein represented herein as SEQ ID NO: 1, the portion at least encoding the IgE binding site of the Fc$_\epsilon$R α chain protein. The double-stranded nucleic acid molecule including both the coding strand having SEQ ID NO: 1 and the complementary non-coding strand (the nucleic acid sequence of which can be readily determined by one skilled in the art and is shown herein as SEQ ID NO:3) is referred to herein as Fc$_\epsilon$R nucleic acid molecule nhFc$_\epsilon$Rα$_{1198}$. Translation of SEQ ID NO: 1 suggests that nucleic acid molecule nhFc$_\epsilon$Rα$_{1198}$ encodes a full-length Fc$_\epsilon$R α chain protein of about 257 amino acids, referred to herein as PhFc$_\epsilon$Rα$_{257}$, represented by SEQ ID NO:2, assuming an open reading frame having an initiation (start) codon spanning from about nucleotide 107 through about nucleotide 109 of SEQ ID NO: 1 and a termination (stop) codon spanning from about nucleotide 878 through about nucleotide 880 of SEQ ID NO: 1. The coding region encoding PhFc$_\epsilon$Rα$_{257}$, including the stop codon, is represented by nucleic acid molecule nhFc$_\epsilon$Rα$_{774}$, having a coding strand with the nucleic acid sequence represented herein as SEQ ID NO:4. SEQ ID NO: 1 encodes a signal peptide of about 25 amino acids as well as a mature protein of about 232 amino acids, denoted herein as PhFc$_\epsilon$Rα$_{232}$, the amino acid sequence of which is represented herein as SEQ ID NO:6. The nucleic acid molecule encoding the apparent mature protein is referred to as nhFc$_\epsilon$Rα$_{699}$, the nucleic acid sequence of the coding strand of which is denoted herein as SEQ ID NO:7. SEQ ID NO: 1 also encodes a hydrophobic transmembrane domain and a cytoplasmic tail which as a group extend from about amino acid 205 to about amino acid 257 of SEQ ID NO:2. Knowledge of these nucleic acid and amino acid sequences allows one skilled in the art to make modifications to the respective nucleic acid molecules and proteins to, for example, develop a $Fc_\epsilon R$ α chain protein with increased solubility and/or a truncated protein (e.g., a peptide) capable of detecting IgE, e.g., $PhFc_\epsilon R\alpha_{197}$ and $PhFc_\epsilon R\alpha_{172}$. Preferred $Fc_\epsilon R$ molecules include $PhFc_\epsilon R\alpha_{257}$, $PhFc_\epsilon R\alpha_{197}$, $PhFc_{\epsilon R\alpha 232}$ and $PhFc_\epsilon R\alpha_{172}$. Preferred nucleic acid molecules to encode a $Fc_\epsilon R$ molecules include $nhFc_\epsilon R\alpha_{774}$, $nhFc_\epsilon R\alpha_{1198}$, $nhFc_{\epsilon \epsilon}R\alpha_{612}$, $nhFc_\epsilon R\alpha_{591}$, $nhFc_\epsilon R\alpha_{699}$ and/or $nhFc_\epsilon R\alpha_{516}$.

Isolated $Fc_\epsilon R$ molecule protein of the present invention can be produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred nucleic acid molecules with which to transform a cell are as disclosed herein for suitable and preferred $Fc_\epsilon R$ nucleic acid molecules per se. Particularly preferred nucleic acid molecules to include in recombinant cells of the present invention include $nhFc_\epsilon R\alpha_{774}$, $nhFc_\epsilon R\alpha_{1198}$, $nhFc_\epsilon R\alpha_{612}$, $nhFc_\epsilon R\alpha_{591}$, $nhFc_\epsilon R\alpha_{699}$ and/or $nhFc_\epsilon R\alpha_{516}$.

Suitable host cells to transform include any cell that can be transformed with a nucleic acid molecule of the present invention. Host cells can be either untransformed cells or cells that are already transformed with at least one nucleic acid molecule. Host cells of the present invention either can be endogenously (i.e., naturally) capable of producing a $Fc_\epsilon R$ molecule protein of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including protozoa and ectoparasite), insect, other animal and plant cells.

Preferably, a recombinant cell is transfected with a recombinant molecule of the present invention which is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. A particularly preferred recombinant molecule includes $pVL-nhFc_\epsilon R\alpha_{612}$. Details regarding the production of $Fc_\epsilon R$ molecule nucleic acid molecule-containing recombinant molecules are disclosed herein. Particularly preferred recombinant cell of the present invention includes *Trichoplusia ni*-$pVL-nhFc_\epsilon R\alpha_{612}$.

A $Fc_\epsilon R$ molecule of the present invention can include chimeric molecules comprising a portion of a $Fc_\epsilon R$ molecule that binds to an IgE and a second molecule that enables the chimeric molecule to be bound to a substrate in such a manner that the $Fc_\epsilon R$ portion binds to IgE in essentially the same manner as a $Fc_\epsilon R$ molecule that is not bound to a substrate. An example of a suitable second molecule includes a portion of an immunoglobulin molecule.

A $Fc_\epsilon R$ molecule of the present invention can be contained in a formulation, herein referred to as a $Fc_\epsilon R$ formulation. For example, a $Fc_\epsilon R$ can be combined with a buffer in which the $Fc_\epsilon R$ is solubilized, and/or a carrier. Suitable buffers and carriers are known to those skilled in the art. Examples of suitable buffers include any buffer in which a $Fc_\epsilon R$ can function to selectively bind to IgE, such as, but not limited to, phosphate buffered saline, water, saline, phosphate buffer, bicarbonate buffer, HEPES buffer (N-2-hydroxyethylpiperazine-N'-2-ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin. Carriers can be in mixed with $Fc_\epsilon R$ or conjugated (i.e., attached) to $Fc_\epsilon R$ in such a manner as to not substantially interfere with the ability of the $Fc_\epsilon R$ to selectively bind to IgE.

A $Fc_\epsilon R$ of the present invention can be bound to the surface of a cell expressing the $Fc_\epsilon R$. A preferred $Fc_\epsilon R$-bearing cell includes a recombinant cell expressing a nucleic acid molecule encoding a human $Fc_\epsilon R$ alpha chain of the present invention. A more preferred recombinant cell of the present invention expresses a nucleic acid molecule that encodes at least one of the following proteins: $PhFc_\epsilon R\alpha_{257}$ and $PhFc_\epsilon R\alpha_{232}$. An even more preferred recombinant cell expresses a nucleic acid molecule including $nhFc_\epsilon R\alpha_{612}$, $nhFc_\epsilon R\alpha_{591}$, $nhFc_\epsilon R\alpha_{699}$ and/or $nhFc_\epsilon R\alpha_{516}$ with a recombinant cell expressing a nucleic acid molecule comprising a nucleic acid sequence including SEQ ID NO: 1 or SEQ ID NO:4, or a nucleic acid molecule comprising an allelic variant of a nucleic acid molecule comprising SEQ ID NO: 1 or SEQ ID NO:4, being even more preferred. An even more preferred recombinant cell is a $RBL-hFc_\epsilon R$ cell.

In addition, a $Fc_\epsilon R$ formulation of the present invention can include not only a $Fc_\epsilon R$ but also one or more additional antigens or antibodies useful in detecting IgE. As used herein, an antigen refers to any molecule capable of being selectively bound by an antibody. As used herein, specific binding of a first molecule to a second molecule refers to the ability of the first molecule to preferentially bind (e.g., having higher affinity higher avidity) to the second molecule when compared to the ability of a first molecule to bind to a third molecule. The first molecule need not necessarily be the natural ligand of the second molecule. Examples of such antibodies include, but are not limited to, antibodies that bind selectively to the constant region of an IgE heavy (i.e., anti-IgE isotype antibody) or antibodies that bind selectively to an IgE having a specific antigen specificity (i.e., anti-IgE idiotypic antibody). Examples of such antigens include any antigen known to induce the production of IgE. Preferred antigens include allergens and parasite antigens. Allergens of the present invention are preferably derived from fungi, trees, weeds, shrubs, grasses, wheat, corn, soybeans, rice, eggs, milk, cheese, bovines (or cattle), poultry, swine, sheep, yeast, fleas, flies, mosquitos, mites, midges, biting gnats, lice, bees, wasps, ants, true bugs or ticks. A suitable flea allergen includes an allergen derived from a flea, in particular flea saliva antigen. A preferred flea allergen includes a flea saliva antigen Preferred flea saliva antigens include antigens such as those disclosed in PCT Patent Publication No. WO 96111271, published Apr. 18, 1996, by Frank et al. (this publication is incorporated by reference herein in its entirety), with flea saliva products and flea saliva proteins being particularly preferred. According to the present invention, a flea saliva protein includes a protein produced by recombinant DNA methods, as well as proteins isolated by other methods disclosed in PCT Patent Publication No. WO 96/11271.

Preferred general allergens include those derived from grass, Meadow Fescue, Curly Dock, plantain, Mexican Firebush, Lamb's Quarters, pigweed, ragweed, sage, elm, cocklebur, Box Elder, walnut, cottonwood, ash, birch, cedar, oak, mulberry, cockroach, Dermataphagoides, Alternaria, Aspergillus, Cladosporiuim, Fusarium, Helminthosporium, Mucor, Penicillium, Pullularia, Rhizopus and/or Tricophyton. More preferred general allergens include those derived from Johnson Grass, Kentucky Blue Grass, Meadow Fescue, Orchard Grass, Perennial Rye Grass, Redtop Grass, Timothy Grass, Bermuda Grass, Brome Grass, Curly Dock, English Plantain, Mexican Firebush, Lamb's Quarters, Rough Pigweed Short Ragweed, Wormwood Sage, American Elm, Common Cocklebur, Box Elder, Black Walnut, Eastern Cottonwood, Green Ash, River Birch, Red Cedar, Red Oak, Red Mulberry, Cockroach, *Dermataphagoides farinae, Alternaria alternata, Aspergillus fumigatus, Cladosporium herbarum, Fusarium vasinfectum, Helminthosporium sativum, Mucor recemosus, Penicillium notatum, Pullularia pullulans, Rhizopus nigricans* and/or Tricophyton spp. Preferred parasite antigens include, but are not limited to, helminth antigens, in particular heartworm antigens, such as Di33 (described in U.S. patent application Ser. No. 08/715,628, filed Sep. 18, 1996, to Grieve et al.). The term "derived from" refers to a natural allergen of such plants or organisms (i.e., an allergen directly isolated from such plants or organisms), as well as, non-natural allergens of such plants or organisms that possess at least one epitope capable of eliciting an immune response against an allergen (e.g., produced using recombinant DNA technology or by chemical synthesis).

The present invention also includes human $Fc_\epsilon R$ mimetopes and use thereof to detect IgE. In accordance with the present invention, a "mimetope" refers to any compound that is able to mimic the ability of a $Fc_\epsilon R$ molecule to bind to IgE. A mimetope can be a peptide that has been modified to decrease its susceptibility to degradation but that still retains IgE-binding activity. Other examples of mimetopes include, but are not limited to, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of synthetic compounds for compounds capable of binding to IgE. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modeling. The predicted mimetope structures can then be produced by, for example, chemical synthesis, recombinant DNA technology, or by isolating a mimetope from a natural source. Specific examples of $Fc_\epsilon R$ mimetopes include anti-idiotypic antibodies, oligonucleotides produced using Selex technology, peptides identified by random screening of peptide libraries and proteins identified by phage display technology.

One embodiment of the present invention is a method to detect non-human IgE which includes the steps of: (a) contacting an isolated human $Fc_\epsilon$ receptor ($Fc_\epsilon R$) molecule with a putative IgE-containing composition under conditions suitable for formation of an $Fc_\epsilon R$ molecule:IgE complex; and (b) detecting levels of IgE by detecting said $Fc_\epsilon R$ molecule:IgE complex. Presence of such a $Fc_\epsilon R$ molecule:IgE complex indicates that the animal is producing IgE. Preferred non-human IgE to detect using a human $Fc_\epsilon R$ molecule include canine IgE, feline IgE and equine IgE. The present method can further include the step of determining whether an IgE complexed with a $Fc_\epsilon R$ molecule is heat labile. Methods to determine heat lability of IgE are disclosed in the Examples section. Preferably, an IgE is heat labile when incubated at about 56° C. for about 4 hours. Without being bound by theory, Applicants believe that heat labile forms of IgE bind to certain allergens and non-heat labile forms of IgE bind to other types of allergens. As such, detection of heat labile IgE compared with non-heat labile IgE can be used to discriminate between allergen sensitivities. For example, Applicants believe that IgE antibodies that bind to certain flea allergens and heartworm allergens are heat labile while IgE antibodies that bind to certain plant allergens are not heat labile. Thus, the presence of non-heat labile IgE can indicate that an animal is sensitive to certain plant allergens but not to certain flea or heartworm allergens. Moreover, Applicants believe that identification of heat labile IgE and non-heat labile IgE using a human $Fc_\epsilon R$ suggests the presence of different sub-populations of IgE that may or may not have substantially similar structures to known IgE. As such, a $Fc_\epsilon R$ molecule of the present invention may be useful for detecting molecules bound by the $Fc_\epsilon R$ molecule but not identical to a known IgE.

As used herein, canine refers to any member of the dog family, including domestic dogs, wild dogs and zoo dogs. Examples of dogs include, but are not limited to, domestic dogs, wild dogs, foxes, wolves, jackals and coyotes. As used herein, a feline refers to any member of the cat family, including domestic cats, wild cats and zoo cats. Examples of cats include, but are not limited to, domestic cats, lions, tigers, leopards, panthers, cougars, bobcats, lynx, jaguars, cheetahs, and servals. As used herein, equine refers to any member of the horse family, including horses, donkeys, mules and zebras.

As used herein, the term "contacting" refers to combining or mixing, in this case a putative IgE-containing composition with a human $Fc_\epsilon R$ molecule. Formation of a complex between a $Fc_\epsilon R$ and an IgE refers to the ability of the $Fc_\epsilon R$ to selectively bind to the IgE in order to form a stable complex that can be measured (i.e., detected). As used herein, the term selectively binds to an IgE refers to the ability of a $Fc_\epsilon R$ of the present invention to preferentially bind to IgE, without being able to substantially bind to other antibody isotypes. Binding between a $Fc_\epsilon R$ and an IgE is effected under conditions suitable to form a complex; such conditions (e.g., appropriate concentrations, buffers, temperatures, reaction times) as well as methods to optimize such conditions are known to those skilled in the art, and examples are disclosed herein. Examples of complex formation conditions are also disclosed in, for example, in Sambrook et al., *Molecular Cloning: A Laboratory Manual*, Cold Spring Harbor Labs Press, 1989, the reference Sambrook et al., ibid., is incorporated by reference herein in its entirety.

As used herein, the term "detecting complex formation" refers to determining if any complex is formed, i.e., assaying for the presence (i.e., existence) of a complex. If complexes are formed, the amount of complexes formed can, but need not be, determined. Complex formation, or selective binding, between $Fc_\epsilon R$ and any IgE in the composition can be measured (i.e., detected, determined) using a variety of methods standard in the art (see, for example, Sambrook et al. ibid.), examples of which are disclosed herein.

In one embodiment, a putative IgE-containing composition of the present method includes a biological sample from an animal. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, central nervous system fluid (CNF), saliva, lymph, nasal secretions, milk and feces. Such a composition of the present method can, but need not be, pretreated to remove at least some of the non-IgE isotypes of immunoglobulin and/or other proteins, such as albumin, present in the fluid. Such removal can include, but is not limited to, contacting the bodily fluid with a material, such as Protein G, to remove IgG antibodies and/or affinity purifying IgE antibodies from other components of the body fluid by exposing the fluid to, for example, Concanavalin A. In another embodiment, a composition includes collected bodily fluid that is pretreated to concentrate immunoglobulin contained in the fluid. For example, immunoglobulin contained in a bodily fluid can be precipitated from other proteins using ammonium sulfate. A preferred composition of the present method is serum.

In another embodiment, a composition of the present method includes an IgE-producing cell. Such a cell can have IgE bound to the surface of the cell and/or can secrete IgE. Examples of such cells include basophil cells and myeloma cells. IgE can be bound to the surface of a cell either directly to the membrane of a cells or bound to a molecule (e.g., an antigen) bound to the surface of the cell.

A complex can be detected in a variety of ways including, but not limited to use of one or more of the following assays: an enzyme-linked immunoassay, a radioimmunoassay, a fluorescence immunoassay, a chemiluminescent assay, a lateral flow assay, an agglutination assay, a particulate-based assay (e.g., using particulates such as, but not limited to, magnetic particles or plastic polymers, such as latex or polystyrene beads), an immunoprecipitation assay, a Bio-Core™ assay (e.g., using colloidal gold) and an immunoblotting assay (e.g., a western blot). Such assays are well known to those skilled in the art. Assays can be used to give qualitative or quantitative results depending on how they are used. Some assays, such as agglutination, particulate separation, and immunoprecipitation, can be observed visually (e.g., either by eye or by a machines, such as a densitometer or spectrophotometer) without the need for a detectable marker. In other assays, conjugation (i.e., attachment) of a detectable marker to the $Fc_\epsilon R$ or to a reagent that selectively binds to the $Fc_\epsilon R$ or to the IgE being detected (described in more detail below) aids in detecting complex formation. Examples of detectable markers include, but are not limited to, a radioactive label, a fluorescent label, a chemiluminescent label, a chromophoric label or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase) and biotin-related compounds or avidin-related compounds (e.g., streptavidin or ImmunoPure® NeutrAvidin). Preferably, biotin is conjugated to an alpha chain of a $Fc_\epsilon R$. Preferably a carbohydrate group of the $Fc_\epsilon R$ alpha chain is conjugated to biotin. A preferred $Fc_\epsilon R$ molecule conjugated to biotin comprises $PhFc_\epsilon R\alpha_{172}$-BIOT (the production of which is described in the Examples section).

In one embodiment, a complex is detected by contacting a putative IgE-containing composition with a $Fc_\epsilon R$ molecule that is conjugated to a detectable marker. A suitable detectable marker to conjugate to a $Fc_\epsilon R$ molecule includes, but is not limited to, a radioactive label, a fluorescent label, a chemiluminescent label or a chromophoric label. A detectable marker is conjugated to a $Fc_\epsilon R$ molecule or a reagent in such a manner as not to block the ability of the $Fc_\epsilon R$ or reagent to bind to the IgE being detected. Preferably, a carbohydrate group of a $Fc_\epsilon R$ is conjugated to biotin.

In another embodiment, a $Fc_\epsilon R$ molecule:IgE complex is detected by contacting a putative IgE-containing composition with a $Fc_\epsilon R$ molecule and then contacting the complex with an indicator molecule. Suitable indicator molecules of the present invention include molecules that can bind to either the $Fc_\epsilon R$ molecule or to the IgE antibody. As such, an indicator molecule can comprise, for example, a $Fc_\epsilon R$ molecule, an antigen, an antibody and a lectin, depending upon which portion of the $Fc_\epsilon R$ molecule:IgE complex being detected. Preferred identifying labeled compounds that are antibodies include, for example, anti-IgE antibodies and anti-$Fc_\epsilon R$ antibodies. Preferred lectins include those lectins that bind to high-mannose groups. More preferred lectins bind to high-mannose groups present on a $Fc_\epsilon R$ molecule of the present invention produced in insect cells. An indicator molecule itself can be attached to a detectable marker of the present invention. For example, an antibody can be conjugated to biotin, horseradish peroxidase, alkaline phosphatase or fluorescein.

In one preferred embodiment, a $Fc_\epsilon R$ molecule:IgE complex is detected by contacting the complex with a reagent that selectively binds to a $Fc_\epsilon R$ molecule of the present invention. Examples of such a reagent includes, but are not limited to, an antibody that selectively binds to a $Fc_\epsilon R$ molecule (referred to herein as an anti-$Fc_\epsilon R$ antibody) or a compound that selectively binds to a detectable marker conjugated to a $Fc_\epsilon R$ molecule. $Fc_\epsilon R$ molecules conjugated to biotin are preferably detected using streptavidin, more preferably using ImmunoPure® NeutrAvidin (available from Pierce, Rockford, Ill.).

In another preferred embodiment, a $Fc_\epsilon R$ molecule:IgE complex is detected by contacting the complex with a reagent that selectively binds to an IgE antibody (referred to herein as an anti-IgE reagent). Examples of such an anti-IgE reagent include, but are not limited to, a secondary antibody that is an anti-isotype antibody (e.g., an antibody that selectively binds to the constant region of an IgE), an antibody-binding bacterial surface protein (e.g., Protein A or Protein G), an antibody-binding cell (e.g., a B cell, a T cell, a natural killer cell, a polymorphonuclear leukocyte cell, a monocyte cell or a macrophage cell), an antibody-binding eukaryotic cell surface protein (e.g., an Fc receptor), and an antibody-binding complement protein. Preferred anti-IgE reagents include, but are not limited to, D9, and CMI antibody #9, CMI antibody #19, CMI antibody #59 and CMI antibody #71 (available from Custom Monoclonal International, West Sacramento, Calif.). In particular, as used herein, an anti-IgE antibody includes not only a complete antibody but also any subunit or portion thereof that is capable of selectively binding to an IgE heavy chain constant region. For example, a portion of an anti-IgE reagent can include an Fab fragment or a F(ab')$_2$ fragment, which are described in detail in Janeway et al., in *Immunobiology, the Immune System in Health and Disease,* Garland Publishing, Inc., NY, 1996 (which is incorporated herein by this reference in its entirety).

In one embodiment a complex can be formed and detected in solution. In another embodiment, a complex can be formed in which one or more members of the complex are immobilized on (e.g., coated onto) a substrate. Immobilization techniques are known to those skilled in the art. Suitable substrate materials include, but are not limited to, plastic, glass, gel, celluloid, paper, PVDF (poly-vinylidene-fluoride), nylon, nitrocellulose, and particulate materials such as latex, polystyrene, nylon, nitrocellulose, agarose and magnetic resin. Suitable shapes for substrate material include, but are not limited to, a well (e.g., microtiter dish well), a plate, a dipstick, a bead, a lateral flow apparatus, a membrane, a filter, a tube, a dish, a celluloid-type matrix, a magnetic particle, and other particulates. A particularly preferred substrate comprises an ELISA plate, a dipstick, a radioimmunoassay plate, agarose beads, plastic beads, latex beads, immunoblot membranes and immunoblot papers. In one embodiment, a substrate, such as a particulate, can include a detectable marker.

A preferred method to detect IgE is an immunosorbent assay. An immunoabsorbent assay of the present invention comprises a capture molecule and an indicator molecule. A capture molecule of the present invention binds to an IgE in such a manner that the IgE is immobilized to a substrate. As such, a capture molecule is preferably immobilized to a substrate of the present invention prior to exposure of the capture molecule to a putative IgE-containing composition. An indicator molecule of the present invention detects the presence of an IgE bound to a capture molecule. As such, an indicator molecule preferably is not immobilized to the same substrate as a capture molecule prior to exposure of the capture molecule to a putative IgE-containing composition.

A preferred immunoabsorbent assay method includes a step of either: (a) binding an $Fc_\epsilon R$ molecule to a substrate prior to contacting a $Fc_\epsilon R$ molecule with a putative IgE-containing composition to form a $Fc_\epsilon R$ molecule-coated substrate; or (b) binding a putative IgE-containing composition to a substrate prior to contacting a $Fc_\epsilon R$ molecule with a putative IgE-containing composition to form a putative IgE-containing composition-coated substrate. Preferably, the substrate includes of a non-coated substrate, a $Fc_\epsilon R$ molecule-coated substrate, an antigen-coated substrate or an anti-IgE antibody-coated substrate.

Both a capture molecule and an indicator molecule of the present invention are capable of binding to an IgE. Preferably, a capture molecule binds to a different region of an IgE than an indicator molecule, thereby allowing a capture molecule to be bound to an IgE at the same time as an indicator molecule. The use of a reagent as a capture molecule or an indicator molecule depends upon whether the molecule is immobilized to a substrate when the molecule is exposed to an IgE. For example, a $Fc_\epsilon R$ molecule of the present invention is used as a capture molecule when the $Fc_\epsilon R$ molecule is bound to a substrate. Alternatively, a $Fc_\epsilon R$ molecule is used as an indicator molecule when the $Fc_\epsilon R$ molecule is not bound to a substrate. Suitable molecule for use as capture molecules or indicator molecules include, but are not limited to, a $Fc_\epsilon R$ molecule of the present invention, an antigen reagent or an anti-IgE antibody reagent of the present invention.

An immunoabsorbent assay of the present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be selected by those of skill in the art. Preferred secondary molecules of the present invention include, an antigen, an anti-IgE idiotypic antibody and an anti-IgE isotypic. Preferred tertiary molecules can be selected by a skilled artisan based upon the characteristics of the secondary molecule. The same strategy is applied for subsequent layers.

In one embodiment, a desired antigen is used as a capture molecule by being immobilized on a substrate, such as a microtiter dish well or a dipstick. Preferred antigens include those disclosed herein. A biological sample collected from an animal is applied to the substrate and incubated under conditions suitable (i.e., sufficient) to allow for antigen:IgE complex formation bound to the substrate (i.e., IgE in a sample binds to an antigen immobilized on a substrate). Excess non-bound material (i.e., material from the biological sample that has not bound to the antigen), if any, is removed from the substrate under conditions that retain antigen:IgE complex binding to the substrate. Preferred conditions are disclosed herein in the Examples section and generally in Sambrook et al., ibid. An indicator molecule that can selectively bind to an IgE bound to the antigen, the indicator molecule can be conjugated to a detectable marker (preferably to an enzyme label, to a colorimetric label, to a fluorescent label, to a radioisotope, or to a ligand such as of the biotin or avidin family), is added to the substrate and incubated to allow formation of a complex between the indicator molecule and the antigen:IgE complex. Excess indicator molecule is removed, a developing agent is added if required, and the substrate is submitted to a detection device for analysis. A preferred indicator molecule for this embodiment is a $Fc_\epsilon R$ molecule, preferably conjugated to biotin, to a fluorescent label or to an enzyme label.

In one embodiment, a $Fc_\epsilon R$ molecule is used as a capture molecule by being immobilized on a substrate, such as a microtiter dish well or a dipstick. A biological sample collected from an animal is applied to the substrate and incubated under conditions suitable to allow for $Fc_\epsilon R$ molecule:IgE complex formation bound to the substrate. Excess non-bound material, if any, is removed from the substrate under conditions that retain $Fc_\epsilon R$ molecule:IgE complex binding to the substrate. An indicator molecule that can selectively bind to an IgE bound to the $Fc_\epsilon R$ is added to the substrate and incubated to allow formation of a complex between the indicator molecule and the $Fc_\epsilon R$ molecule:IgE complex. Preferably, the indicator molecule is conjugated to a detectable marker (preferably to an enzyme label, to a colorimetric label, to a fluorescent label, to a radioisotope, or to a ligand such as of the biotin or avidin family). Excess indicator molecule is removed, a developing agent is added if required, and the substrate is submitted to a detection device for analysis. A preferred indicator molecule for this embodiment is an antigen that will bind to IgE in the biological sample or an anti-IgE isotype or idiotype antibody, either preferably being conjugated to fluorescein or biotin.

In one embodiment, an anti-IgE antibody (e.g., isotype or idiotype specific antibody) is used as a capture molecule by being immobilized on a substrate, such as a microtiter dish well or a dipstick. A biological sample collected from an animal is applied to the substrate and incubated under conditions suitable to allow for anti-IgE antibody:IgE complex formation bound to the substrate. Excess non-bound material, if any, is removed from the substrate under conditions that retain anti-IgE antibody:IgE complex binding to the substrate. A $Fc_\epsilon R$ molecule is added to the substrate and incubated to allow formation of a complex between the Fc$_\epsilon$R molecule and the anti-IgE antibody:IgE complex. Preferably, the Fc$_\epsilon$R molecule is conjugated to a detectable marker (preferably to biotin, an enzyme label or a fluorescent label). Excess Fc$_\epsilon$R molecule is removed, a developing agent is added if required, and the substrate is submitted to a detection device for analysis.

In one embodiment, an immunosorbent assay of the present invention does not utilize a capture molecule. In this embodiment, a biological sample collected from an animal is applied to a substrate, such as a microtiter dish well or a dipstick, and incubated under conditions suitable to allow for IgE binding to the substrate. Any IgE present in the bodily fluid is immobilized on the substrate. Excess non-bound material, if any, is removed from the substrate under conditions that retain IgE binding to the substrate. A Fc$_\epsilon$R molecule is added to the substrate and incubated to allow formation of a complex between the Fc$_\epsilon$R molecule and the IgE. Preferably, the Fc$_\epsilon$R molecule is conjugated to a detectable marker (preferably to biotin, an enzyme label or a fluorescent label). Excess Fc$_\epsilon$R molecule is removed, a developing agent is added if required, and the substrate is submitted to a detection device for analysis.

Another preferred method to detect IgE is a lateral flow assay, examples of which are disclosed in U.S. Pat. No. 5,424,193, issued Jun. 13, 1995, by Pronovost et al.; U.S. Pat. No. 5,415,994, issued May 16, 1995, by Imrich et al; WO 94/29696, published Dec. 22, 1994, by Miller et al.; and WO 94/01775, published Jan. 20, 1994, by Pawlak et al.; each of these patent publications is incorporated by reference herein in its entirety. In one embodiment, a biological sample is placed in a lateral flow apparatus that includes the following components: (a) a support structure defining a flow path; (b) a labeling reagent comprising a bead conjugated to an antigen, the labeling reagent being impregnated within the support structure in a labeling zone; and (c) a capture reagent comprising an IgE-binding composition. Preferred antigens include those disclosed herein. The capture reagent is located downstream of the labeling reagent within a capture zone fluidly connected to the labeling zone in such a manner that the labeling reagent can flow from the labeling zone into the capture zone. The support structure comprises a material that does not impede the flow of the beads from the labeling zone to the capture zone. Suitable materials for use as a support structure include ionic (i.e., anionic or cationic) material. Examples of such a material include, but are not limited to, nitrocellulose (NC), PVDF, carboxymethylcellulose (CM). The support structure defines a flow path that is lateral and is divided into zones, namely a labeling zone and a capture zone. The apparatus can further comprise a sample receiving zone located along the flow path, more preferably upstream of the labeling reagent. The flow path in the support structure is created by contacting a portion of the support structure downstream of the capture zone, preferably at the end of the flow path, to an absorbent capable of absorbing excess liquid from the labeling and capture zones.

In this embodiment, the biological sample is applied to the sample receiving zone which includes a portion of the support structure. The labeling zone receives the sample from the sample receiving zone which is directed downstream by the flow path. The labeling zone comprises the labeling reagent that binds to IgE. A preferred labeling reagent is an antigen conjugated, either directly or through a linker, to a plastic bead substrate, such as to a latex bead. The substrate also includes a detectable marker, preferably a colorimetric marker. Typically, the labeling reagent is impregnated to the support structure by drying or lyophilization. The sample structure also comprises a capture zone downstream of the labeling zone. The capture zone receives labeling reagent from the labeling zone which is directed downstream by the flow path. The capture zone contains the capture reagent, in this case a Fc$_\epsilon$R molecule, as disclosed above, that immobilizes the IgE complexed to the antigen in the capture zone. The capture reagent is preferably fixed to the support structure by drying or lyophilizing. The labeling reagent accumulates in the capture zone and the accumulation is assessed visually or by an optical detection device.

In another embodiment, a lateral flow apparatus used to detect IgE includes: (a) a support structure defining a flow path; (b) a labeling reagent comprising a Fc$_\epsilon$R molecule as described above, the labeling reagent impregnated within the support structure in a labeling zone; and (c) a capture reagent comprising an antigen, the capture reagent being located downstream of the labeling reagent within a capture zone fluidly connected to the labeling zone in such a manner that the labeling reagent can flow from the labeling zone into the capture zone. The apparatus preferably also includes a sample receiving zone located along the flow path, preferably upstream of the labeling reagent. The apparatus preferably also includes an absorbent located at the end of the flow path.

One embodiment of the present invention is an inhibition assay in which the presence of IgE in a putative IgE-containing composition is determined by adding such composition to a Fc$_\epsilon$R molecule of the present invention and an isolated IgE known to bind to the Fc$_\epsilon$R molecule. The absence of binding of the Fc$_\epsilon$R molecule to the known IgE indicating the presence of IgE in the putative IgE-containing composition.

The present invention also includes kits to detect IgE based on each of the disclosed detection methods. One embodiment is a kit to detect IgE comprising a human Fc$_\epsilon$ receptor (Fc$_\epsilon$R) molecule and a means for detecting an IgE including canine IgE, feline IgE and/or equine IgE. Suitable and preferred Fc$_\epsilon$R molecules are disclosed herein. Suitable means of detection include compounds disclosed herein that bind to either the Fc$_\epsilon$R molecule or to an IgE. A preferred kit of the present invention further comprises a detection means including one or more antigens disclosed herein, an antibody capable of selectively binding to an IgE disclosed herein and/or a compound capable of binding to a detectable marker conjugated to a Fc$_\epsilon$R molecule (e.g., avidin, streptavidin and ImmunoPure® NeutrAvidin when the detectable marker is biotin). Such antigens preferably induce IgE antibody production in animals including canines, felines and/or equines.

A preferred embodiment of a kit of the present invention is a flea allergen kit comprising a flea allergen such as those disclosed herein. A particularly preferred flea allergen for use with a flea allergen kit includes a flea saliva product or a flea saliva protein.

Another preferred kit of the present invention is a general allergen kit comprising an allergen common to all regions of the United States and a human Fc$_\epsilon$R molecule of the present invention. As used herein, a "general allergen" kit refers to a kit comprising allergens that are found substantially throughout the United States (i.e., essentially not limited to certain regions of the United States). A general allergen kit provides an advantage over regional allergen kits because a single kit can be used to test an animal located in most geographical locations on the United States. Suitable and preferred general allergens for use with a general allergen kit of the present invention include those general allergens disclosed herein.

Another preferred kit of the present invention is a food allergen kit comprising a food allergen including beef, chicken, pork, a mixture of fish, such as cod, halibut or and tuna, egg, milk, Brewer's yeast, whole wheat, corn, soybean, cheese and rice, and a human $Fc_\epsilon R$ molecule of the present invention. Preferably, the beef, chicken, pork, fish, corn and rice, are cooked.

A preferred kit of the present invention includes those in which the allergen is immobilized to a substrate. If a kit comprises two or more antigens, the kit can comprise one or more compositions, each composition comprising one antigen. As such, each antigen can be tested separately. A kit can also contain two or more diagnostic reagents for IgE, additional isolated IgE antigens and/or antibodies as disclosed herein. Particularly preferred are kits used in a lateral flow assay format. It is within the scope of the present invention that a lateral flow assay kit can include one or more lateral flow assay apparatuses. Multiple lateral flow apparatuses can be attached to each other at one end of each apparatus, thereby creating a fan-like structure.

In particular, a method and kit of the present invention are useful for diagnosing abnormal conditions in animals that are associated with changing levels of IgE. Particularly preferred conditions to diagnose include allergies, parasitic infections and neoplasia. For example, a method and kit of the present invention are particularly useful for detecting flea allergy dermatitis (FAD), when such method or kit includes the use of a flea saliva antigen. FAD is defined as a hypersensitive response to fleabites. Preferably, a putative IgE-containing composition is obtained from an animal suspected of having FAD. Preferred animals include those disclosed herein, with dogs and cats being more preferred. In addition, methods and kits of the present invention are particularly useful for detecting helminth infection, in particular heartworm infection, when such methods or kits include the use of a helminth antigen, such as Di33. Preferably, a putative IgE-containing composition is obtained from an animal suspected of having a helminth infection. Preferred animals include those disclosed herein, with dogs and cats being more preferred.

The following examples are provided for the purposes of illustration and are not intended to limit the scope of the present invention.

EXAMPLES

Example 1

This example describes the construction of a recombinant baculovirus expressing a truncated portion of the a-chain of the human $Fc_\epsilon$ receptor.

Recombinant molecule $pVL-nhFc_\epsilon R\alpha_{612}$, containing a nucleic acid molecule encoding the extracellular domain of the $Fc_\epsilon R$ α chain, operatively linked to baculovirus polyhedron transcription control sequences was produced in the following manner. A cDNA clone encoding the full-length alpha chain (α chain) of the human $Fc_\epsilon$ receptor was obtained from Dr. Jean-Pierre Kinet (Harvard University, Cambridge, Mass.). The cDNA clone included an about 1198 nucleotide insert, referred to herein as $nhFc_\epsilon R\alpha_{1198}$. The nucleic acid sequence of the coding strand of $nhFc_\epsilon R\alpha_{1198}$ is denoted herein as SEQ ID NO: 1. Translation of SEQ ID NO: 1 indicates that nucleic acid molecule $nhFc_\epsilon R\alpha_{1198}$ encodes a full-length human $Fc_\epsilon$ receptor α chain protein of about 257 amino acids, referred to herein as $PhFc_\epsilon R\alpha_{257}$, having amino acid sequence SEQ ID NO:2, assuming an open reading frame in which the initiation codon spans from about nucleotide 107 through about nucleotide 109 of SEQ ID NO: 1 and the termination codon spans from about nucleotide 878 through about nucleotide 880 of SEQ ID NO: 1. The complement of SEQ ID NO: 1 is represented herein by SEQ ID NO:3. The proposed mature protein (i.e., $Fc_\epsilon R\alpha$ chain from which the signal sequence has been cleaved), denoted herein as $PhFc_\epsilon R\alpha_{232}$, contains about 232 amino acids which is represented herein as SEQ ID NO:6. The nucleic acid molecule encoding $PhFc_\epsilon R\alpha_{232}$ is denoted herein as $nhFc_\epsilon R\alpha_{696}$, the coding strand of which is represented by SEQ ID NO:7.

To produce a secreted form of the extracellular domain of the $Fc_\epsilon R$ α chain, the hydrophobic transmembrane domain and the cytoplasmic tail of the $Fc_\epsilon R$ α chain encoded by $nhFc_\epsilon R\alpha_{1198}$ were removed as follows. A $Fc_\epsilon R$ α chain extracellular domain nucleic acid molecule-containing fragment of about 612 nucleotides was PCR amplified from $nhFc_\epsilon R\alpha_{1198}$ using a forward primer EJH 040 containing a BamHI site, having the nucleic acid sequence 5'CGC GGA TCC TAT AAT ATG GCT CCT GCC ATG G3' (denoted SEQ ID NO:8) and a reverse primer IgE ANTI-SENSE containing an EcoRI site, having the nucleic acid sequence 5'GGC GAA TTC TTA AGC TTT TAT TAC AG3' ( denoted herein as SEQ ID NO:9). The resulting PCR product was digested with BamHI and EcoRI to produce $nhFc_\epsilon R\alpha_{612}$. Nucleic acid molecule $nhFc_\epsilon R\alpha_{612}$ contained an about 591 nucleotide fragment encoding the extracellular domain of the human $Fc_\epsilon R$ α chain, extending from about nucleotide 107 to about nucleotide 697 of SEQ ID NO 1, denoted herein as nucleic acid molecule $nhFc_\epsilon R\alpha_{591}$, the coding strand of which has a nucleic acid sequence denoted SEQ ID NO: 10. Translation of SEQ ID NO: 10 indicates that nucleic acid molecule $nhFc_\epsilon R\alpha_{612}$ encodes a $Fc_\epsilon R$ protein of about 197 amino acids, referred to herein as $PhFc_\epsilon R\alpha_{197}$, having amino acid sequence SEQ ID NO: 11. Nucleic acid molecule $nhFc_\epsilon R\alpha_{612}$ encodes a secretable form of the human $Fc_\epsilon R$ α chain which does not possess a leader sequence, which is denoted herein as $PhFc_\epsilon R\alpha_{172}$ having amino acid sequence SEQ ID NO:13. The coding region for $PhFc_\epsilon R\alpha_{172}$ is denoted $nhFc_\epsilon R\alpha_{516}$, the coding strand of which has a nucleic acid sequence denoted SEQ ID NO: 12. The complement of SEQ ID NO: 12 is represented herein by SEQ ID NO: 14.

In order to produce a baculovirus recombinant molecule capable of directing the production of $PhFc_\epsilon R\alpha_{197}$, the nucleic acid molecule $nhFc_\epsilon R\alpha_{612}$ was subcloned into unique BamHI and EcoRI sites of pVL1392 baculovirus shuttle plasmid (available from Pharmingen, San Diego, Calif.) to produce a recombinant molecule referred to herein as $pVL-nhFc_\epsilon R\alpha_{612}$. The resultant recombinant molecule $pVL-nhFc_\epsilon R\alpha_{612}$ was verified for proper insert orientation by restriction mapping.

Example 2

This example describes the production of $PhFc_\epsilon R\alpha_{172}$ protein.

The recombinant molecule $pVL-nhFc_\epsilon R\alpha_{612}$ was co-transfected with a linear Baculogold baculovirus DNA (available from Pharmingen) into *Trichoplusia ni* cells (available from Invitrogen Corp., San Diego, Calif.; High Five™ cells) using the following method. About 1.5 liter cultures of serum-free ex-Cell Medium (available from Invitrogen) were seeded with about $1\times10^6$ cells per ml of medium. The Trichoplusia ni cells were infected with recombinant molecule pVL-nh$Fc_\epsilon R\alpha_{612}$ at a multiplicity of infection (MOI) of about 2 to about 5 particle forming units (pfu) per cell to produce recombinant cell *Trichoplusia ni*-pVL-nh$Fc_\epsilon R\alpha_{612}$. The infection was allowed to proceed at a controlled temperature of 27° C. for 48 hours, to produce recombinant protein Ph$Fc_\epsilon R\alpha_{172}$. Following infection, cells were separated from the medium by centrifugation, and the medium was frozen at −70° C.

Ph$Fc_\epsilon R\alpha_{172}$was purified from the culture medium described immediately above by affinity chromatography using an IgE antibody produced by the myeloma cell line U266DI (American Tissue Type Catalogue No. TIB 196) linked to sepharose 4B. The amino acid composition and N-terminal amino acid sequence of the affinity purified Ph$Fc_\epsilon R\alpha_{172}$ were determined using methods standard in the art. The results indicated that Ph$Fc_\epsilon R\alpha_{172}$ was properly processed by the *Trichoplusia ni* cells.

Example 3

This example describes the biotinylation of a recombinant human $Fc_\epsilon R$ alpha chain protein.

Affinity purified recombinant protein Ph$Fc_\epsilon R\alpha_{172}$, prepared as described above in Example 2, was biotinylated as follows. About 440 micrograms ($\mu$g) of Ph$Fc_\epsilon R\alpha_{172}$ were diluted in about 1.5 milliliter (ml) of acetate buffer (0.1 M NaAc, pH 5.5) containing about 200 microliter ($\mu$l) of 0.1 M $NaIO_4$. The mixture was incubated for about 20 minutes, on ice, and about 2 $\mu$l of glycerol was added following the incubation. The mixture was then dialyzed against about 2 liters of acetate buffer in a 3 ml Slide-A-Lyzer cassette (available from Pierce, Rockford, Ill.), 2 times for about 2 hours each time. About 3.72 $\mu$g of biotin-LC-hydrazide (available from Pierce) was dissolved in about 200 $\mu$l of dimethylsulfoxide (DMSO) and injected into the cassette. The cassette was then rocked at room temperature for about 2 hours. Following the incubation, the mixture containing recombinant protein and biotin dialyzed 3 times, a first time for about 18 hours and two times for about 2 hours, each time at 5° C. against phosphate buffered saline. The biotinylated protein was recovered from the dialysis, and is referred to herein as Ph$Fc_\epsilon R\alpha_{172}$-BIOT.

Example 4

This example describes detection of canine IgE in a solid-phase ELISA using Ph$Fc_\epsilon R\alpha_{172}$-BIOT.

Wells of two Immulon II microtiter plates (available from Dynatech, Alexandria, Va.) were coated with duplicate samples of about 100 $\mu$l/well of various concentrations of purified canine IgE as denoted in FIG. 1. The canine IgE was obtained from a canine IgE producing hybridoma, such as heterohybridoma 2.39 (described in Gebhard et al., *Immunology* 85:429434, 1995) and was diluted in a CBC buffer (15 mM $Na_2CO_3$ and 34.8 mM $NaHCO_3$, pH 9.6. The coated plates were incubated overnight at 4° C. Following incubation, the canine IgE-containing solution was removed from each plate, and the plates were blotted dry. The plates were then blocked using about 200 $\mu$l/well of 0.25% bovine serum albumin (BSA) contained in phosphate buffered saline (PBSB) for about 1 hour at room temperature. The plates were then washed four times with 0.05% Tween-20 in PBS (PBST) using an automatic washer (available from Dynatech). Experimental samples consisting of about 100 $\mu$l/well of a 1:4000 dilution of 40 $\mu$g/ml Ph$Fc_\epsilon R\alpha_{172}$-BIOT (about 145 $\mu$g/ml; described in Example 3), contained in PBSB with 0.05% Tween-20 (PBSBT) were added to each well of one plate coated with canine IgE. Control samples consisting of about 100 p1] of biotinylated anti-canine IgE monoclonal antibody D9 (supplied by Dr. DeBoer, U. of Wisconsin, Madison, Wis.) were added to each well of the other plate coated with canine IgE. The plates were incubated for 1 hour at room temperature and then washed four times with PBST. About 100 $\mu$l of about 0.25 ug/ml streptavidin conjugated to horseradish peroxidase (available from Kirkegaard and Perry Laboratories (KPL), Gaithersburg, Md.; diluted in PBST) was added to each well that received experimental or control samples. The plates were then incubated for 1 hour at room temperature and washed four times with PBST. About 100 $\mu$l of TMB substrate (available from available from KPL), that had been pre-warmed to room temperature, was added. Plates were then incubated for 10 minutes at room temperature and then about 100 $\mu$l/well of Stop Solution (available from KPL) was added. Optical densities of wells were read on a Spectramax Microtiter Plate (available from Molecular Devices Inc.) reader at 450 nm within 10 minutes of adding the stop solution.

The results shown in FIG. 1 indicate that the alpha chain of human $Fc_\epsilon R$ detects the presence of canine IgE (closed circles) in a solid-phase assay in a similar manner as the control antibody that binds specifically to canine IgE (D9; open circles).

Example 5

This example describes detection of plant allergen-specific canine IgE using Ph$Fc_\epsilon R\alpha_{172}$-BIOT.

Multiple wells of an Immulon II microtiter plate (available from Dynatech) were coated with either about 100 $\mu$l/well of 1 $\mu$g/ml of Kentucky Blue Grass allergen or about 100 $\mu$l/well of about 1 $\mu$g/ml of Green Ash allergen (both available from Greer Inc., Lenoir, N.C.) both diluted in CBC buffer. The plate was incubated overnight at 4° C. The plate was blocked and washed as described in Example 4. Two different pools of canine sera were then added to the antigen-coated wells. The first pool consisted of sera isolated from 8 dogs reported to be allergen reactive. The second pool consisted of sera isolated from 8 dogs reported to be allergen non-reactive. Each pool of sera was diluted 1:10 or 1:100 in PBST. About 100 $\mu$l of each concentration of each diluted sera sample was added to the wells and incubated for 1 hour at room temperature. The plate was then washed four times with PBST. About 100 $\mu$l/well of a 1:4000 dilution of 40 $\mu$g/ml Ph$Fc_{63}R\alpha_{172}$-BIOT (described in Example 3), contained in PBSBT was added to the antigen-coated wells. The plate was incubated for 1 hour at room temperature. The plate was then washed four times with PBST. About 100 $\mu$l/well of about 0.25 $\mu$g/ml of neutravidin conjugated to horseradish peroxidase (available from Pierce) contained in PBSBT, was added. The plate was incubated for 1 hour at room temperature. The plate was then washed and the presence of neutravidin bound to the plate detected using the method described in Example 4.

The results shown in FIG. 2 indicate that the alpha chain of human $Fc_\epsilon R$ detects the presence of canine IgE antibodies that bind specifically to a common grass allergen or to a common tree allergen. In addition, detection of canine IgE antibodies is dose dependent.

Example 6

This example describes detection of total canine IgE using Ph$Fc_\epsilon R\alpha_{172}$-BIOT.

Multiple wells of an Immulon II microtiter plate (available from Dynatech) were coated with about 100

μl/well of about 1 μg/ml CMI anti-canine IgE antibody #6 (available from Custom Monoclonals International, West Scramento, Calif.) diluted in CBC buffer. The plate was incubated overnight at 4° C. The plate was blocked and washed as described in Example 4. About 100 μl/well of a 1:60 dilution in PBSBT of sera samples from a variety of sources were then added to multiple wells coated with anti-IgE antibody. The samples included:(l) serum from a dog known to be allergic to flea saliva; (2) serum from dogs infected with D. immitis; (3) and (4) a pool of dog sera from defined as canine allergy calibrators (available from Bio-Products DVM, Tempe, Ariz.); (5) pools of dog sera containing antibodies that have low binding to Kentucky Blue Grass allergen; (6) pools of dog sera that have high binding to Kentucky Blue Grass allergen; (7) a pool of dog sera from dogs known to be allergic to flea saliva, the sample was heat inactivated (at 56° C. for 4 hours); (8) a pool of dog sera from dogs known to be allergic to flea saliva; or (9) a pool of dog sera from dogs raised in a barrier facility (i.e., negative control). A set of positive control samples consisting of IgE derived from the canine heterohybridoma described in Example 4 were also added to the plate to generate a standard curve. The plate was incubated for 1 hour at room temperature and then washed four times with PBST. The presence of canine IgE was detected using either about 100 μl/well of a 1:4000 dilution of 40 μg/ml PhFc$_\epsilon$Rα$_{172}$-BIOT (described in Example 3) or about 100 μl/well of about 1 82 g/ml CMI anti-canine IgE antibody #19 (available from Custom Monoclonals International), both contained in PBSBT. The plate was incubated for 1 hour at room temperature. The plate was then washed, contacted with about 0.25 μg/ml streptavidin conjugated to horseradish peroxidase, washed again, and the presence of streptavidin bound to the plate was detected using the method described in Example 4. The optical density readings obtained for the control samples were used to generate a standard curve that was used to determine the total IgE bound to wells that had received test samples.

Figure 3:
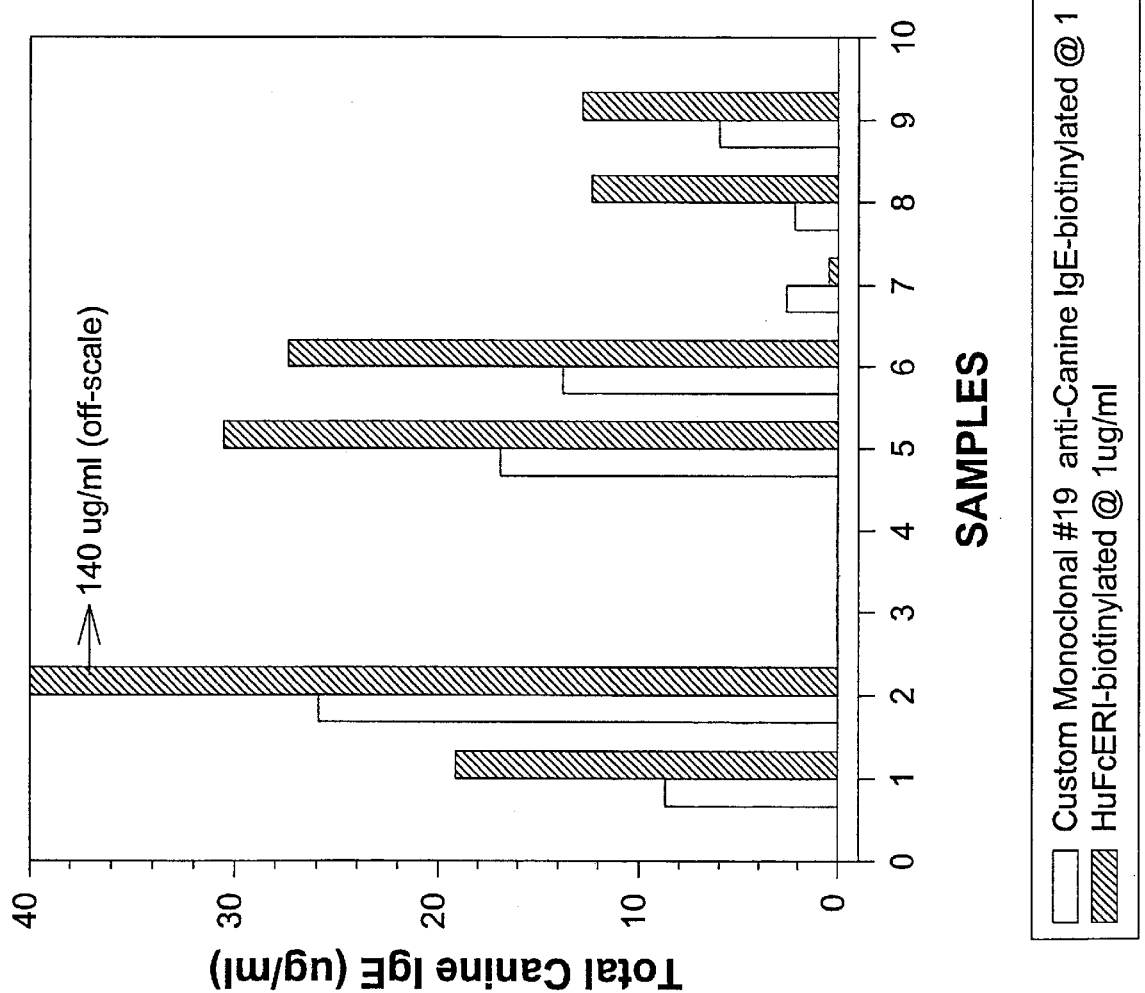
FIG. 3 depicts ELISA results using biotinylated alpha chain of human Fc$_\epsilon$R to detect human or canine IgE antibodies.

The results shown in FIG. 3 indicate that canine IgE from a variety of dog sera are detected using the alpha chain of human Fc$_\epsilon$R in a manner similar to using an antibody that binds specifically to canine IgE The absence of detectable amounts of IgE in the heat treated sample (Sample 7) indicates that the antibody detected by PhFc$_\epsilon$Rα$_{172}$-BIOT is IgE. In addition, the results indicate that PhFC$_\epsilon$Rα$_{172}$-BIOT is an effective reagent for detecting IgE that binds to allergen Kentucky Blue Grass, Samples 5 and 6), as well as a parasite antigen (D. Immitis, Sample 2).

Example 7

This example describes detection of canine IgE in dog sera isolated from dogs known to be allergic to flea saliva, using PhFc$_\epsilon$Rα$_{172}$-BIOT.

Figure 4:
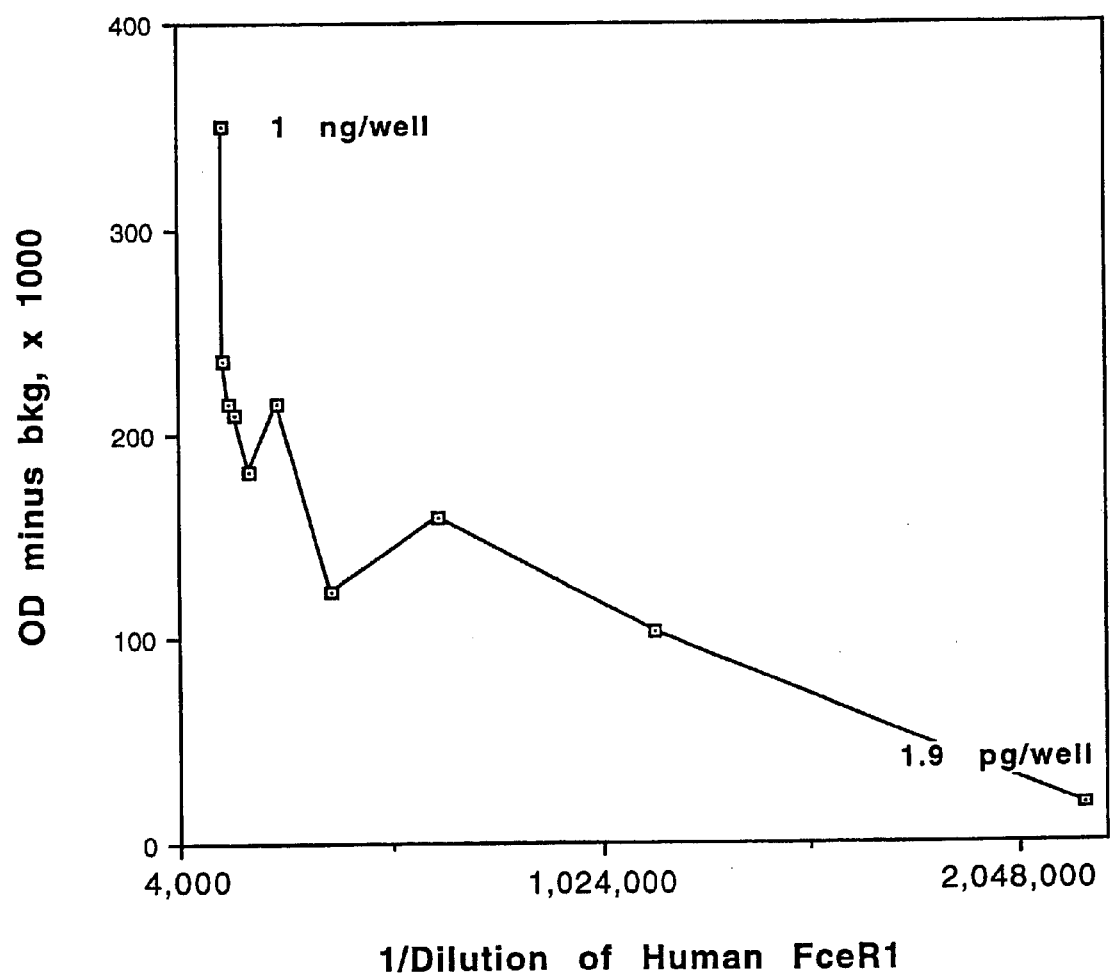
FIG. 4 depicts ELISA results using biotinylated alpha chain of human Fc$_\epsilon$R to detect flea allergen-specific canine IgE antibodies.

Multiple wells of an Immulon II microtiter plate were coated with about 100 μl/well of varying concentrations of flea saliva recombinant protein fspN (described in PCT Patent Publication No. WO 96/11271, ibid.; concentrations shown in FIG. 4) diluted in CBC buffer. The plate was incubated overnight at 4° C. The plate was then blocked and washed as described in Example 4. About 100 μl/well of a 1:10 dilution in PBSBT of a pool of sera isolated from dogs known to produce IgE that binds specifically to flea saliva. Some wells did not receive dog sera so that background binding levels could be determined. The plate was incubated for 1 hour at room temperature and then washed four times with PBST. About 100 μl/well of a 1:4000 dilution of 40 μg/ml PhFc$_\epsilon$Rα$_{172}$-BIOT (described in Example 3) contained in PBSBT was added. The plate was incubated for 1 hour at room temperature. The plate was then washed, contacted with about 0.25 ug/ml streptavidin-conjugated to horseradish peroxidase, washed again, and the presence of streptavidin bound to the plate was detected using the method described in Example 4.

The results shown in FIG. 4 indicate that canine IgE that binds specifically to a flea saliva antigen is detected using the alpha chain of human Fc$_\epsilon$R.

Example 8

This example describes detection of total canine IgE in dog sera isolated from dogs known to be allergic to flea saliva, heartworm-infected dogs and specific pathogen free (SPF) dogs, using PhFc$_\epsilon$Rα$_{172}$-BIOT.

Multiple wells of an Immulon II microtiter plate were coated with about 100 μl/well of about 1 μg/ml CMI anti-canine IgE antibody #6 (available from Custom Monoclonals International) in CBC buffer. The plate was incubated overnight at 4° C. The plate was blocked and washed as described in Example 4. About 100 μl/well of different samples of IgE-containing fluids in PBSBT were added to multiple wells coated with the anti-canine IgE antibody. The samples included: (1) 100 μg/ml of canine IgE purified from the heterohybridoma described in Example 4; (2) a 1:10 dilution of a pool of sera from dogs known to be allergic to flea saliva, (3) a 1:10 dilution of the same sera pool as in (2) but heat inactivated; (4) a 1:10 dilution of serum from a dog known to have clinical flea allergy dermatitis (dog CPO2); (5) a 1:10 dilution of heat inactivated CPO2 serum; (6) a 1:10 dilution of serum from a heartworm-infected dog (dog 417); (7) a 1:10 dilution of heat inactivated 417 serum; (8) a 1:10 dilution of a pool of sera from heartworm-infected dogs; (9) a 1:10 dilution of the same sera pool as in (8) but heat inactivated; and (10) a pool of sera from dogs raised in a barrier facility. Each sample was diluted in PBSBT. The plate was incubated for 1 hour at room temperature and then washed four times with PBST. About 100 μl/well of a 1:4000 dilution of 40 μg/ml PhFc$_\epsilon$Rα$_{172}$-BIOT (described in Example 3) in PBSBT was added. The plate was incubated for 1 hour at room temperature. The plate was then washed, contacted with about 0.25 ug/ml streptavidin-conjugated to horseradish peroxidase, washed again, and the presence of streptavidin bound to the plate was detected using the method described in Example 4.

Figure 5:
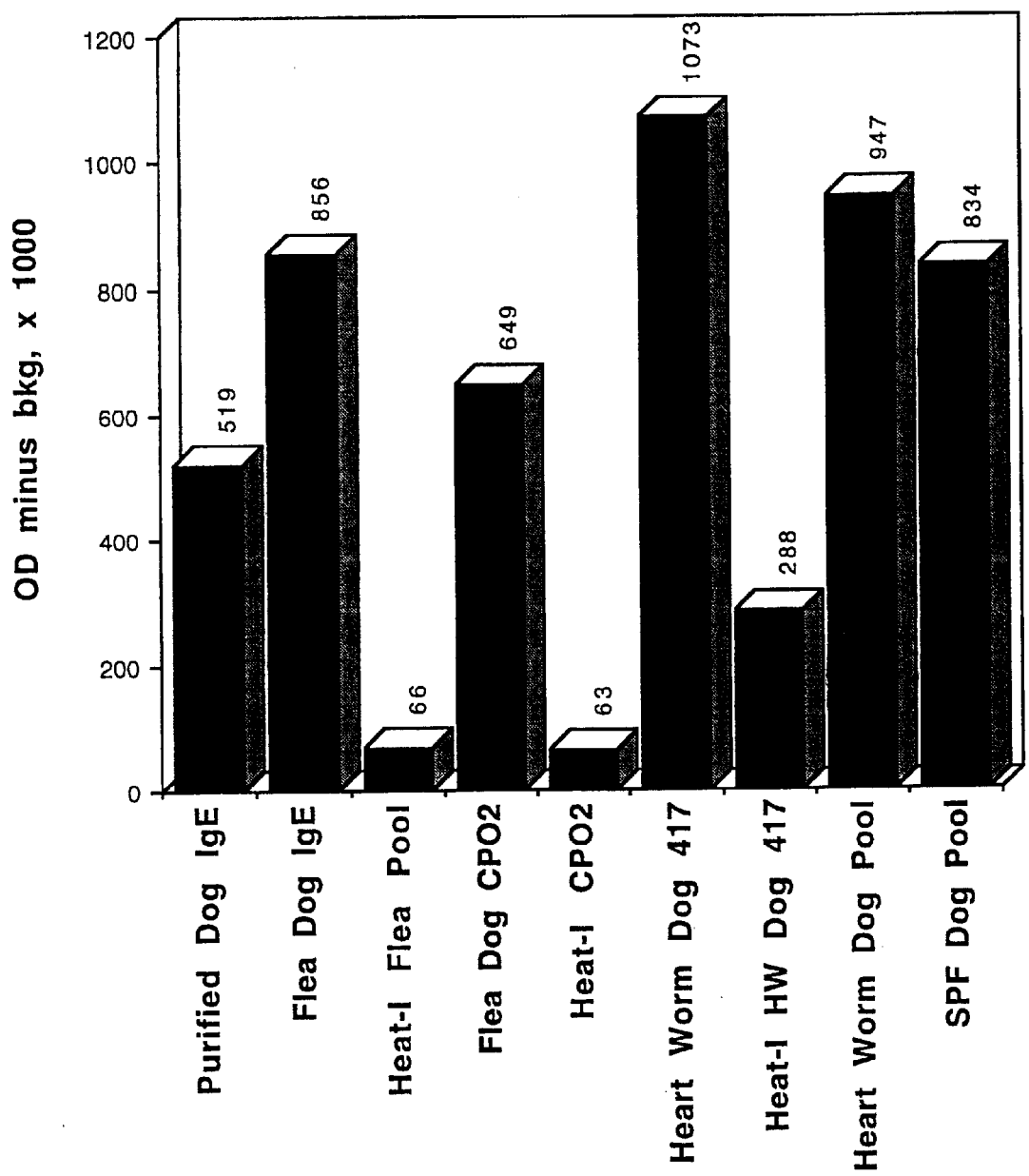
FIG. 5 depicts ELISA results using biotinylated alpha chain of human Fc$_\epsilon$R to detect flea allergen-specific and heartworm antigen-specific canine IgE antibodies.

The results shown in FIG. 5 indicate that canine IgE from dogs allergic to flea saliva and from dogs infected with heartworm are detected using the alpha chain of human Fc$_\epsilon$R. In addition, the absence of colorimetric signal in samples of heat inactivated sera indicates that antibody bound to the anti-IgE antibody and detected by Fc$_\epsilon$R alpha chain is an epsilon isotype antibody and not another isotype.

Example 9

This example describes detection of IgE that specifically binds to flea saliva, using PhFc$_\epsilon$Rα$_{172}$-BIOT.

Multiple wells of an Immulon II microtiter plate were coated with about 100 μl/well of about 0.1 μg/ml of flea saliva collected using the method described in PCT Patent Publication No. WO 96/11271, ibid., in CBC buffer. The plate was incubated, blocked and washed as described in Example 4. The IgE-containing samples described in Example 8 were then applied to the flea saliva coated plate. The plate was then treated using the method described in Example 8.

Figure 6:
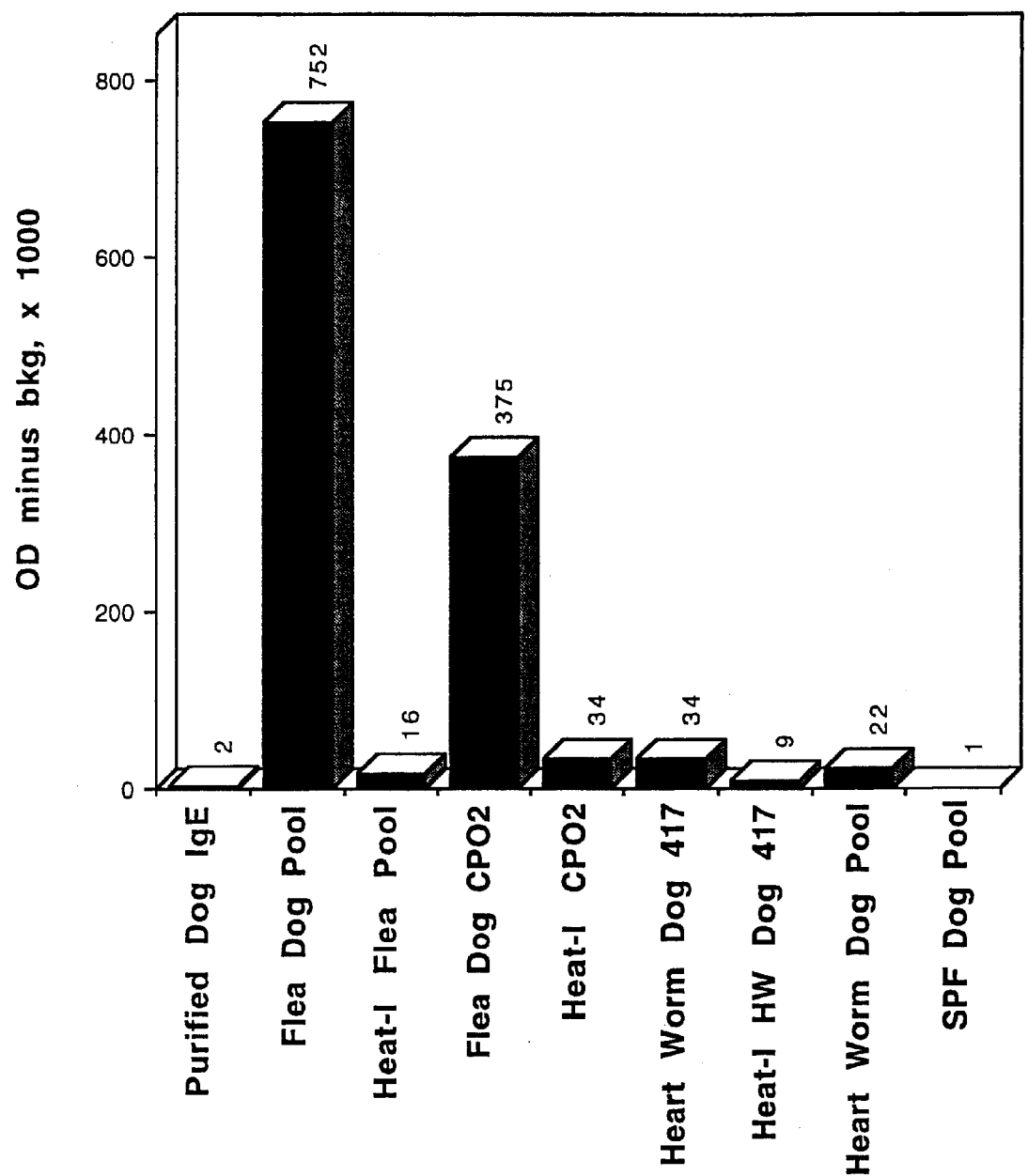
FIG. 6 depicts ELISA results using biotinylated alpha chain of human Fc$_\epsilon$R to detect flea saliva-specific canine IgE antibodies.

The results shown in FIG. 6 indicate that canine IgE that binds specifically to flea saliva, contained in serum, is detected using the alpha chain of human Fc$_\epsilon$R. In addition, the absence of colorimetric signal in samples of heat inactivated serum indicates that antibody bound to the flea saliva protein and detected by Fc$_\epsilon$R alpha chain is an epsilon isotype antibody.

Example 10

This example describes the detection of feline IgE using PhFc$_\epsilon$R$\alpha_{172}$-BIOT.

Multiple wells of an Immulon II microtiter plate were coated with about 100 μl/well of about 10 μg/ml Di33 protein (described in U.S. patent application Ser. No. 08/715,628, ibid.) or 10 μg/ml crude homogenate of heartworm, both in CBC buffer. Crude homogenate of heartworm is the clarafied supernatant of adult heartworms homogenized in PBS. The plate was incubated overnight at 4° C. The plate was blocked and washed as described in Example 4. Serum samples from 2 heartworm infected cats were then added to Di33-coated wells and to heartworm antigen-coated wells. About 100 μl/well of a 1:10 dilution in PBSBT of sera from heartworm-infected cat # AXH3 or from cat #MGC2 were added to the plate. Negative control samples consisting of serum from pre-infection bleeds of cat #AXH3 and cat# MGC2 were also added to the plate at a dilution of 1:10 in PBSBT. A positive control sample consisting of a pool of sera from heartworm-infected dogs was also added to the plate at a dilution of 1:10 in PBSBT. The plate was incubated for 1 hour at room temperature and then washed four times with PBST. About 100 μl/well of a 1:4000 dilution of 40 μg/ml PhFc$_\epsilon$R$\alpha_{172}$-BIOT (described in Example 3) in PBSBT was added. The plate was incubated for 1 hour at room temperature. The plate was then washed, contacted with 1:4000 dilution of a 0.5 mg/ml solution of streptavidin-conjugated to horseradish peroxidase, washed again, and the presence of streptavidin bound to the plate was detected using the method described in Example 4.

Figure 7:
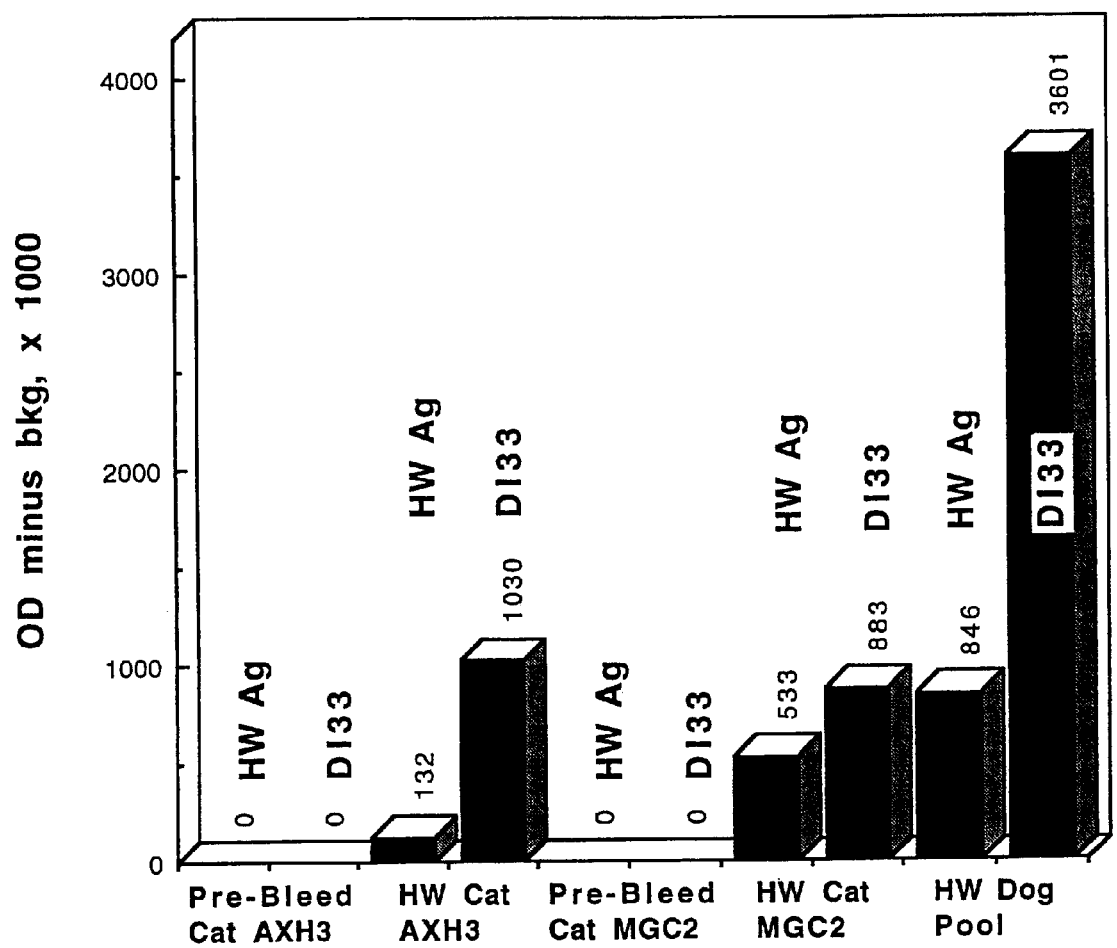
FIG. 7 depicts ELISA results using biotinylated alpha chain of human Fc$_\epsilon$R to detect heartworm antigen-specific feline IgE antibodies.

The results shown in FIG. 7 indicate that feline IgE that binds specifically to crude homogenate of heartworm or Di33 protein is detected using the alpha chain of human Fc$_\epsilon$R.

Example 11

This example describes detection of feline IgE using PhFc$_\epsilon$R$\alpha_{172}$-BIOT.

Multiple wells of an Immulon II microtiter plate were coated with Di33 as described in Example 10, in CBC buffer. The plate was incubated overnight at 4° C. The plate was blocked and washed as described in Example 4. Serum samples from 2 heartworm infected cats were then added to Di33-coated wells. About 100 μl/well of a 1:10 dilution in PBSBT of serum from heartworm-infected cat # MGC2 and a pool of sera from heartworm-infected cats, as well as heat inactivated samples of each of these sera, were added to the plate. A positive control sample consisting of a pool of sera from heartworm-infected dogs was also added to the plate at a dilution of 1:10 in PBSBT. The plate was incubated for 1 hour at room temperature and then washed four times with PBST. About 100 μl/well of a 1:4000 dilution of 40 μg/ml PhFc$_\epsilon$R$\alpha_{172}$-BIOT (described in Example 3) in PBSBT was added. The plate was incubated for 1 hour at room temperature. The plate was then washed, contacted with streptavidin-conjugated to horseradish peroxidase, washed again, and the presence of streptavidin bound to the plate was detected using the method described in Example 4.

Figure 8:
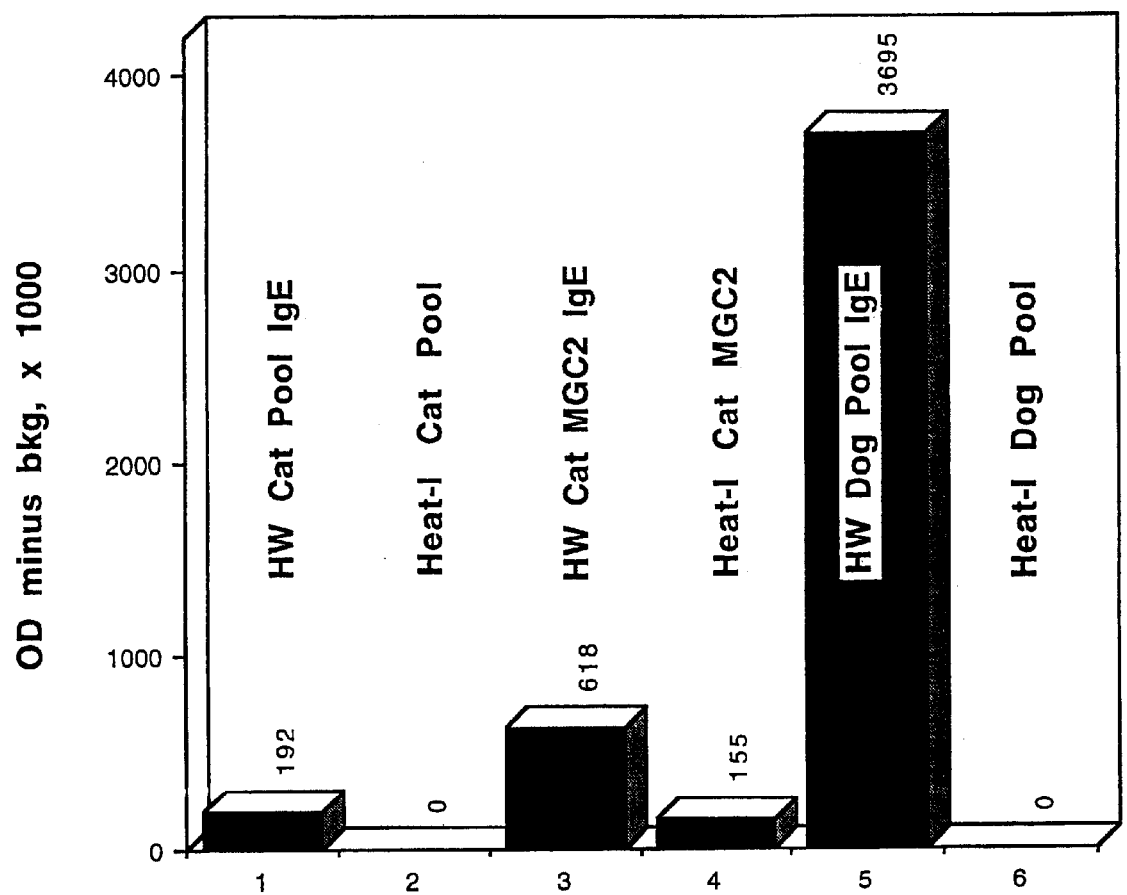
FIG. 8 depicts ELISA results using biotinylated alpha chain of human Fc$_\epsilon$R to detect heartworm antigen-specific feline IgE antibodies.

The results shown in FIG. 8 indicate that feline IgE from heartworm-infected cats that specifically binds to the heart-worm antigen Di33 is detected using the alpha chain of human Fc$_\epsilon$R. In addition, the absence of colorimetric signal in samples of heat inactivated sera indicates that antibody bound to the Di33 protein and detected by Fc$_\epsilon$R alpha chain is an epsilon isotype antibody.

Example 12

This example describes detection of equine IgE in a solid-phase ELISA using PhFc$_\epsilon$R$\alpha_{172}$-BIOT.

Horse sera from a horse known to be allergic to certain allergens and horse sera from a horse known not to be allergic the same allergens, were assayed for the presence of IgE using PhFc$_\epsilon$R$\alpha_{172}$-BIOT as follows. A North Atlantic/Ohio Valley Regional Panel plate of a Canitec™ Allergen-Specific IgE Kit (available from BioProducts DVM) was blocked and washed as described in Example 4. Two samples of about 1:10 dilutions of the two horse sera were prepared using PBSBT. The two samples were added to the blocked plate and the plate was incubated for I hour at room temperature. The plate was washed as described in Example 4. About 100 μl/well of a 1:4000 dilution of 40 μg/ml PhFc$_\epsilon$R$\alpha_{172}$-BIOT (described in Example 3), contained in PBSBT was added to each well.

The plate was then washed, contacted with 1:4000 dilution of a 0.5 mg/ml solution of streptavidin-conjugated to horseradish peroxidase, washed again, and the presence of streptavidin bound to the plate was detected using the method described in Example 4.

Figure 9:
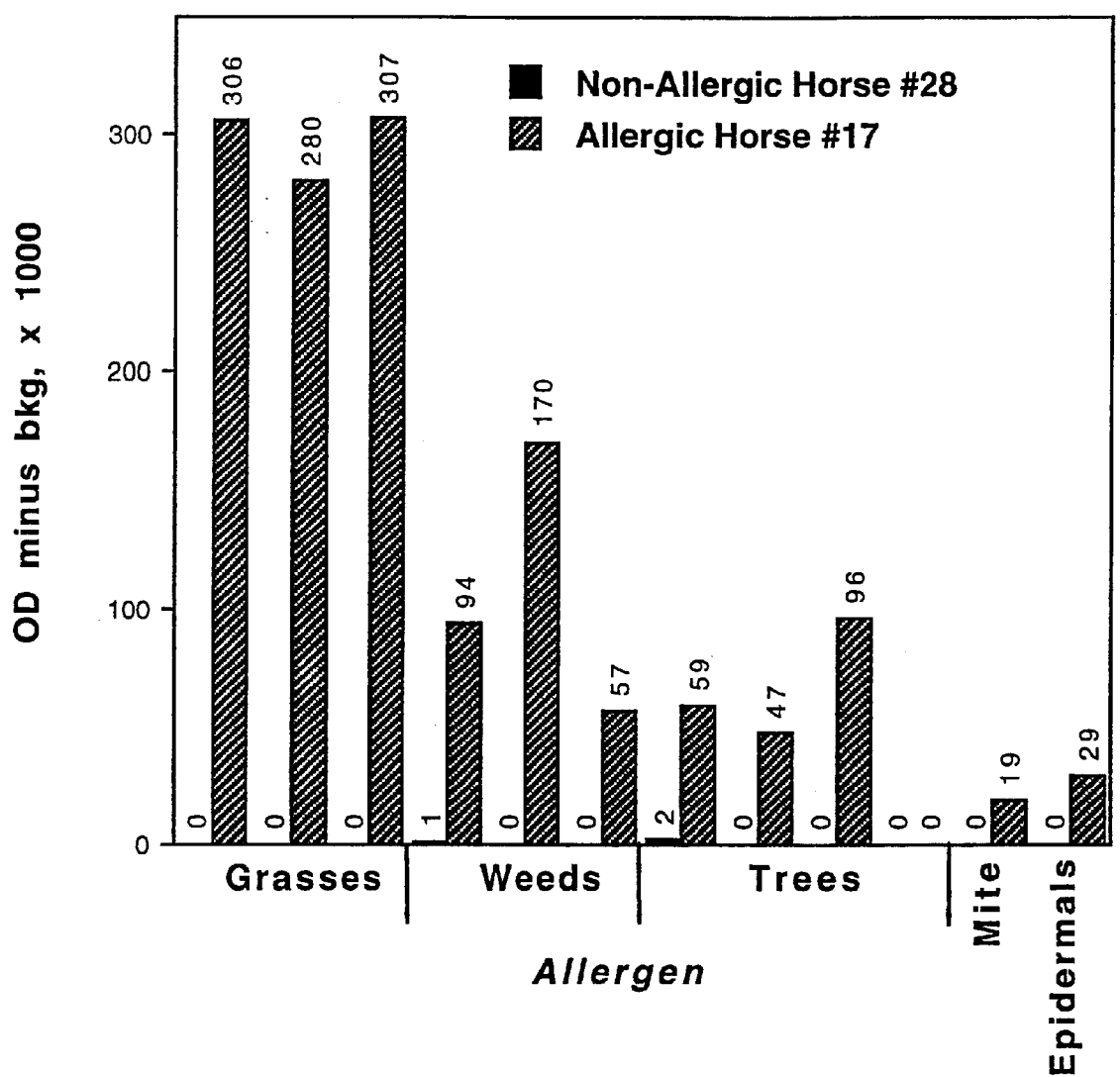
FIG. 9 depicts ELISA results using biotinylated alpha chain of human Fc$_\epsilon$R to detect antigen-specific equine IgE antibodies.

The results shown in FIG. 9 indicate that equine IgE from a horse known to be allergic to certain allergens specifically binds to certain plant and mite allergens is detected using the alpha chain of human Fc$_\epsilon$R.

Example 13

This example describes detection of canine IgE in a solid-phase ELISA using basophilic cells transfected with human Fc$_\epsilon$R alpha chain.

Rat basophilic leukemia (RBL) cells transfected with a nucleic acid molecule encoding a human Fc$_\epsilon$R alpha chain (referred to herein as RBL-hFc$_\epsilon$R cells; described in Miller et al., *Science* 244:334–337, 1989) were used to detect canine IgE as follows. About 4×10$^4$ RBL-hFc$_\epsilon$R cells contained in Earles Modified Eagles Medium containing 10% fetal bovine serum (EMEM-FBS) were added to each well of 96-well flat bottom tissue culture plates. The RBL-hFc$_\epsilon$R cells were incubated overnight at 37° C. Following the incubation the plates were washed 4 times with PBST. The cells were then fixed for about 2 minutes using about 200 μl per well of absolute alcohol at room temperature. The plates were then washed 8 times with PBST to remove residual alcohol.

Serial dilutions in EMEM-FBS (concentrations shown in FIG. 10) were prepared using a pool of sera from dogs infected with heartworm. Serial dilutions in EMEM-FBS (concentrations shown in FIG. 11) were prepared using a pool of sera from dogs sensitized to flea saliva. Additional samples were prepared in which both pools of sera were heat inactivated for about 4 hours at 56° C. The heat treated samples were diluted as described above.

About 100 μl of each dilution of each serum sample was added to separate wells containing fixed RBL-hFc$_\epsilon$R cells and the plates were incubated at 37° C. for about 1 hour. Following the incubation, the plates were washed 4 times with PBST. About 5 μg of a murine IgG monoclonal antibody anit-canine IgE antibody (i.e., Custom Monoclonal Antibody #71; available from Custom Monoclonal International) in 100 µl of EMEM-FBS was added to each well. The plates were incubated for about 30 minutes at 37° C. Following the incubation, the plates were washed 4 times with PBST. About 100 ng of horseradish peroxidase labelled donkey anti-murine IgG (available from Jackson Laboratories, Westgrove, Pa.) in 100 µl of EMEM-FBS was added to each well, and the plates were incubated for about 30 minutes at room temperature. Following the incubation, the plates were washed 4 times with PBST. The presence of anti-murine IgG bound to the plates thereby indicating the ability of RBL-hFc$_\epsilon$R cells to bind to canine IgE was detected using the method described in Example 4.

Figure 10:
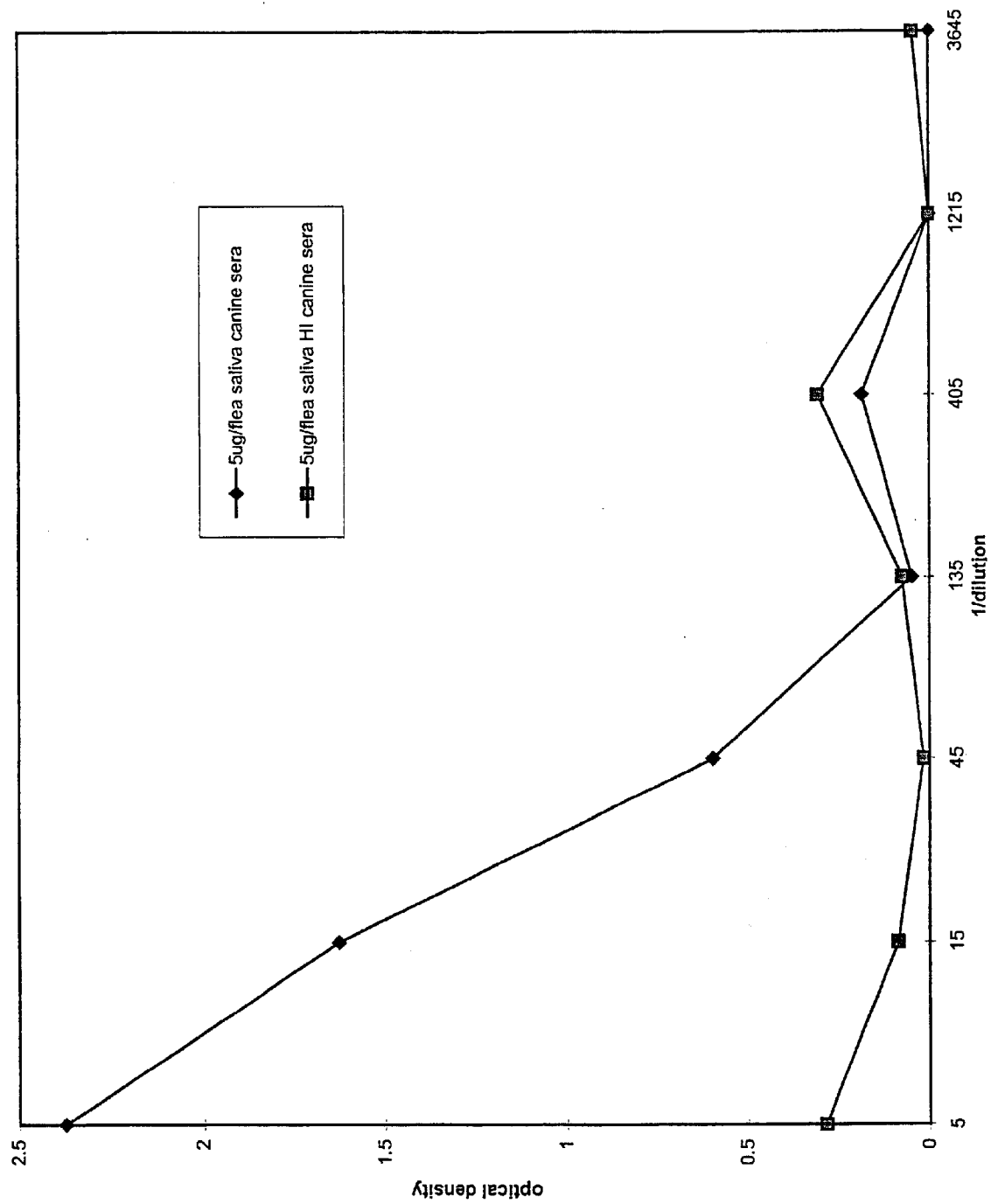
FIG. 10 depicts ELISA results using basophilic leukemia cells expressing alpha chain of human Fc$_\epsilon$R to detect canine IgE antibodies in sera from heartworm-infected dogs.
Figure 11:
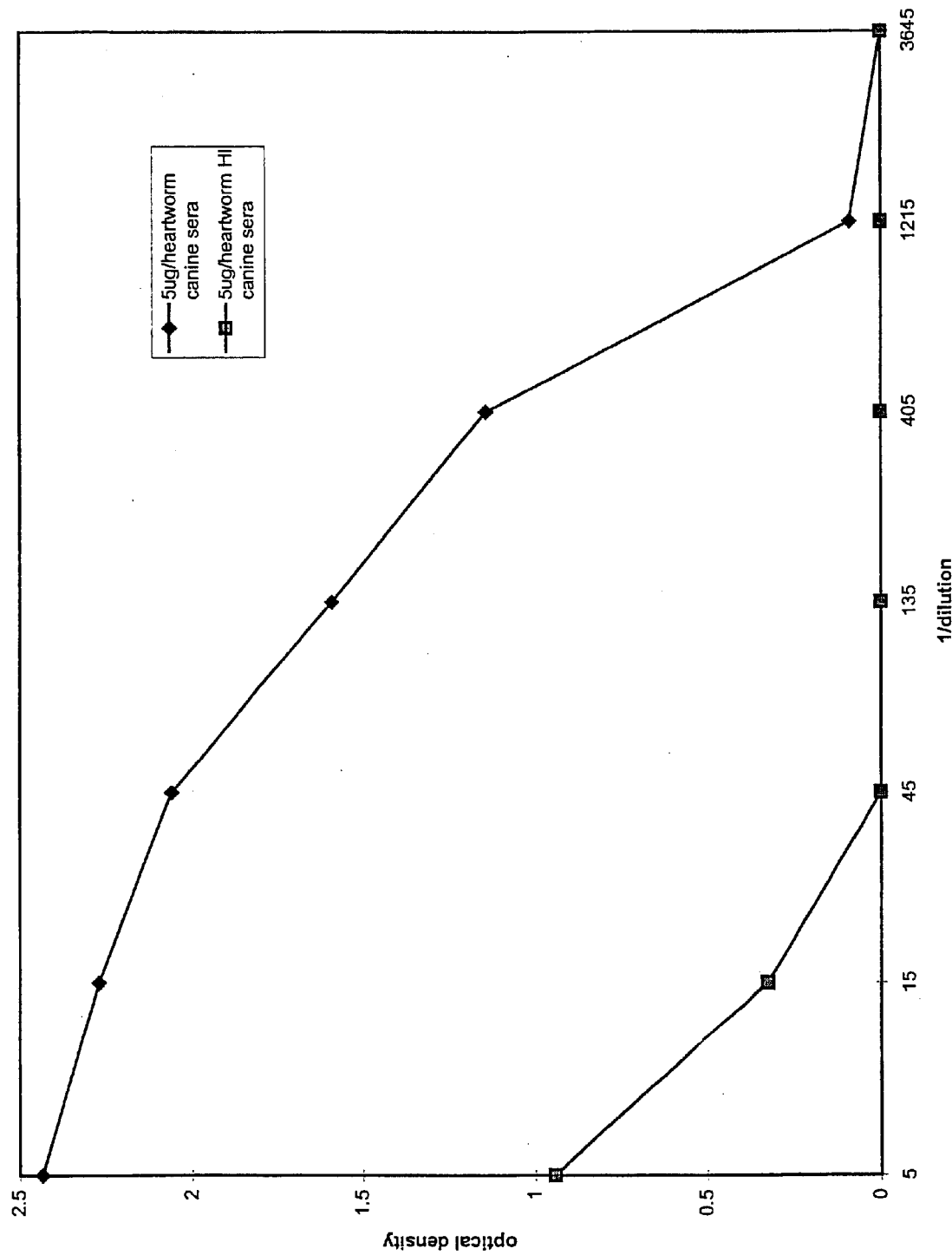
FIG. 11 depicts ELISA results using basophilic leukemia cells expressing alpha chain of human Fc$_\epsilon$R to detect canine IgE antibodies in sera from flea saliva sensitized dogs.

The results shown in FIG. 10 indicate that canine IgE from heartworm-infected dogs (♦) is detected using RBL-h Fc$_\epsilon$R cells expressing the alpha chain of human Fc$_\epsilon$R. In addition, the absence of colorimetric signal in samples of heat inactivated samples of such sera (■) indicates that antibody detected by the Fc$_\epsilon$R alpha chain on the RBL-h Fc$_\epsilon$R cells is an epsilon isotype antibody. Similarly, the results shown in FIG. 11 indicate that canine IgE from dogs sensitized with flea saliva (♦) is detected using RBL-h Fc$_\epsilon$R cells expressing the alpha chain of human Fc$_\epsilon$R. In addition, the absence of colorimetric signal in samples of heat inactivated samples of such sera (■) indicates that antibody detected by the Fc$_\epsilon$R alpha chain on the RBL-h Fc$_\epsilon$R cells is an epsilon isotype antibody.

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1198 nucleotides
      (B) TYPE: nucleic acid
      (C) STRANDEDNESS: single
      (D) TOPOLOGY: linear (ii) MOLECULE TYPE: cDNA (iii) FEATURE:
      (A) NAME/KEY: CDS
      (B) LOCATION: 107..877

(iv) SEQUENCE DESCRIPTION: SEQ ID NO:1:

```
TACTAAGAGT CTCCAGCATC CTCCACCTGT CTACCACCGA GCATGGGCCT ATATTTGAAG        60

CCTTAGATCT CTCCAGCACA GTAAGCACCA GGAGTCCATG AAGAAG ATG GCT CCT          115
                                                  Met Ala Pro
                                                    1

GCC ATG GAA TCC CCT ACT CTA CTG TGT GTA GCC TTA CTG TTC TTC GCT         163
Ala Met Glu Ser Pro Thr Leu Leu Cys Val Ala Leu Leu Phe Phe Ala
      5                  10                  15

CCA GAT GGC GTG TTA GCA GTC CCT CAG AAA CCT AAG GTC TCC TTG AAC         211
Pro Asp Gly Val Leu Ala Val Pro Gln Lys Pro Lys Val Ser Leu Asn
 20                  25                  30                  35

CCT CCA TGG AAT AGA ATA TTT AAA GGA GAG AAT GTG ACT CTT ACA TGT         259
Pro Pro Trp Asn Arg Ile Phe Lys Gly Glu Asn Val Thr Leu Thr Cys
             40                  45                  50

AAT GGG AAC AAT TTC TTT GAA GTC AGT TCC ACC AAA TGG TTC CAC AAT         307
Asn Gly Asn Asn Phe Phe Glu Val Ser Ser Thr Lys Trp Phe His Asn
                 55                  60                  65

GGC AGC CTT TCA GAA GAG ACA AAT TCA AGT TTG AAT ATT GTG AAT GCC         355
Gly Ser Leu Ser Glu Glu Thr Asn Ser Ser Leu Asn Ile Val Asn Ala
             70                  75                  80

AAA TTT GAA GAC AGT GGA GAA TAC AAA TGT CAG CAC CAA CAA GTT AAT         403
Lys Phe Glu Asp Ser Gly Glu Tyr Lys Cys Gln His Gln Gln Val Asn
         85                  90                  95

GAG AGT GAA CCT GTG TAC CTG GAA GTC TTC AGT GAC TGG CTG CTC CTT         451
Glu Ser Glu Pro Val Tyr Leu Glu Val Phe Ser Asp Trp Leu Leu Leu
100                 105                 110                 115

CAG GCC TCT GCT GAG GTG GTG ATG GAG GGC CAG CCC CTC TTC CTC AGG         499
Gln Ala Ser Ala Glu Val Val Met Glu Gly Gln Pro Leu Phe Leu Arg
                120                 125                 130
```

-continued

```
TGC CAT GGT TGG AGG AAC TGG GAT GTG TAC AAG GTG ATC TAT TAT AAG          547
Cys His Gly Trp Arg Asn Trp Asp Val Tyr Lys Val Ile Tyr Tyr Lys
        135                 140                 145

GAT GGT GAA GCT CTC AAG TAC TGG TAT GAG AAC CAC AAC ATC TCC ATT          595
Asp Gly Glu Ala Leu Lys Tyr Trp Tyr Glu Asn His Asn Ile Ser Ile
        150                 155                 160

ACA AAT GCC ACA GTT GAA GAC AGT GGA ACC TAC TAC TGT ACG GGC AAA          643
Thr Asn Ala Thr Val Glu Asp Ser Gly Thr Tyr Tyr Cys Thr Gly Lys
        165                 170                 175

GTG TGG CAG CTG GAC TAT GAG TCT GAG CCC CTC AAC ATT ACT GTA ATA          691
Val Trp Gln Leu Asp Tyr Glu Ser Glu Pro Leu Asn Ile Thr Val Ile
180                 185                 190                 195

AAA GCT CCG CGT GAG AAG TAC TGG CTA CAA TTT TTT ATC CCA TTG TTG          739
Lys Ala Pro Arg Glu Lys Tyr Trp Leu Gln Phe Phe Ile Pro Leu Leu
                200                 205                 210

GTG GTG ATT CTG TTT GCT GTG GAC ACA GGA TTA TTT ATC TCA ACT CAG          787
Val Val Ile Leu Phe Ala Val Asp Thr Gly Leu Phe Ile Ser Thr Gln
                215                 220                 225

CAG CAG GTC ACA TTT CTC TTG AAG ATT AAG AGA ACC AGG AAA GGC TTC          835
Gln Gln Val Thr Phe Leu Leu Lys Ile Lys Arg Thr Arg Lys Gly Phe
                230                 235                 240

AGA CTT CTG AAC CCA CAT CCT AAG CCA AAC CCC AAA AAC AAC TGA              880
Arg Leu Leu Asn Pro His Pro Lys Pro Asn Pro Lys Asn Asn
        245                 250                 255

TATAATTACT CAAGAAATAT TTGCAACATT AGTTTTTTTC CAGCATCAGC AATTGCTACT        940

CAATTGTCAA ACACAGCTTG CAATATACAT AGAAACGTCT GTGCTCAAGG ATTTATAGAA       1000

ATGCTTCATT AAACTGAGTG AAACTGGTTA AGTGGCATGT AATAGTAAGT GCTCAATTAA       1060

CATTGGTTGA ATAAATGAGA GAATGAATAG ATTCATTTAT TAGCATTTGT AAAAGAGATG       1120

TTCAATTTCA ATAAAATAAA TATAAAACCA TGTAACAGAA TGCTTCTGAG TAAAAAAAAA       1180

AAAAAAAAAA AAAAAAAA                                                     1198

(2) INFORMATION FOR SEQ ID NO:2:

(i) SEQUENCE CHARACTERISTICS:
        (A) LENGTH: 257 amino acids
        (B) TYPE: amino acid
        (D) TOPOLOGY: linear (ii) MOLECULE TYPE: protein (iii) SEQUENCE DESCRIPTION: SEQ ID NO:2:

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
                100                 105                 110

Leu Leu Leu Gln Ala Ser Ala Glu Val Val Met Glu Gly Gln Pro Leu
            115                 120                 125
```

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn (2) INFORMATION FOR SEQ ID NO:3:

(i) SEQUENCE CHARACTERISTICS:
        (A) LENGTH: 1198 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:3:

```
TTTTTTTTTT TTTTTTTTTT TTTTTTTACT CAGAAGCATT CTGTTACATG GTTTTATATT      60

TATTTTATTG AAATTGAACA TCTCTTTTAC AAATGCTAAT AAATGAATCT ATTCATTCTC     120

TCATTTATTC AACCAATGTT AATTGAGCAC TTACTATTAC ATGCCACTTA ACCAGTTTCA     180

CTCAGTTTAA TGAAGCATTT CTATAAATCC TTGAGCACAC ACGTTTCTAT GTATATTGCA     240

AGCTGTGTTT GACAATTGAG TAGCAATTGC TGATGCTGGA AAAAAACTAA TGTTGCAAAT     300

ATTTCTTGAG TAATTATATC AGTTGTTTTT GGGGTTTGGC TTAGGATGTG GGTTCAGAAG     360

TCTGAAGCCT TTCCTGGTTC TCTTAATCTT CAAGAGAAAT GTGACCTGCT GCTGAGTTGA     420

GATAAATAAT CCTGTGTCCA CAGCAAACAG AATCACCACC AACAATGGGA TAAAAAATTG     480

TAGCCAGTAC TTCTCACGCG GAGCTTTTAT TACAGTAATG TTGAGGGGCT CAGACTCATA     540

GTCCAGCTGC CACACTTTGC CCGTACAGTA GTAGGTTCCA CTGTCTTCAA CTGTGGCATT     600

TGTAATGGAG ATGTTGTGGT TCTCATACCA GTACTTGAGA GCTTCACCAT CCTTATAATA     660

GATCACCTTG TACACATCCC AGTTCCTCCA ACCATGGCAC CTGAGGAAGA GGGGCTGGCC     720

CTCCATCACC ACCTCAGCAG AGGCCTGAAG GAGCAGCCAG TCACTGAAGA CTTCCAGGTA     780

CACAGGTTCA CTCTCATTAA CTTGTTGGTG CTGACATTTG TATTCTCCAC TGTCTTCAAA     840

TTTGGCATTC ACAATATTCA AACTTGAATT TGTCTCTTCT GAAAGGCTGC CATTGTGGAA     900

CCATTTGGTG GAACTGACTT CAAAGAAATT GTTCCCATTA CATGTAAGAG TCACATTCTC     960

TCCTTTAAAT ATTCTATTCC ATGGAGGGTT CAAGGAGACC TTAGGTTTCT GAGGGACTGC    1020

TAACACGCCA TCTGGAGCGA AGAACAGTAA GGCTACACAC AGTAGAGTAG GGATTCCAT    1080

GGCAGGAGCC ATCTTCTTCA TGGACTCCTG GTGCTTACTG TGCTGGAGAG ATCTAAGGCT    1140

TCAAATATAG GCCCATGCTC GGTGGTAGAC AGGTGGAGGA TGCTGGAGAC TCTTAGTA     1198
```

-continued (2) INFORMATION FOR SEQ ID NO:4:

(i) SEQUENCE CHARACTERISTICS:
        (A) LENGTH: 774 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..774

(iv) SEQUENCE DESCRIPTION: SEQ ID NO:4:

```
ATG GCT CCT GCC ATG GAA TCC CCT ACT CTA CTG TGT GTA GCC TTA CTG        48
Met Ala Pro Ala Met Glu Ser Pro Thr Leu Leu Cys Val Ala Leu Leu
 1               5                  10                  15

TTC TTC GCT CCA GAT GGC GTG TTA GCA GTC CCT CAG AAA CCT AAG GTC        96
Phe Phe Ala Pro Asp Gly Val Leu Ala Val Pro Gln Lys Pro Lys Val
             20                  25                  30

TCC TTG AAC CCT CCA TGG AAT AGA ATA TTT AAA GGA GAG AAT GTG ACT       144
Ser Leu Asn Pro Pro Trp Asn Arg Ile Phe Lys Gly Glu Asn Val Thr
         35                  40                  45

CTT ACA TGT AAT GGG AAC AAT TTC TTT GAA GTC AGT TCC ACC AAA TGG       192
Leu Thr Cys Asn Gly Asn Asn Phe Phe Glu Val Ser Ser Thr Lys Trp
     50                  55                  60

TTC CAC AAT GGC AGC CTT TCA GAA GAG ACA AAT TCA AGT TTG AAT ATT       240
Phe His Asn Gly Ser Leu Ser Glu Glu Thr Asn Ser Ser Leu Asn Ile
 65                  70                  75                  80

GTG AAT GCC AAA TTT GAA GAC AGT GGA GAA TAC AAA TGT CAG CAC CAA       288
Val Asn Ala Lys Phe Glu Asp Ser Gly Glu Tyr Lys Cys Gln His Gln
                 85                  90                  95

CAA GTT AAT GAG AGT GAA CCT GTG TAC CTG GAA GTC TTC AGT GAC TGG       336
Gln Val Asn Glu Ser Glu Pro Val Tyr Leu Glu Val Phe Ser Asp Trp
            100                 105                 110

CTG CTC CTT CAG GCC TCT GCT GAG GTG GTG ATG GAG GGC CAG CCC CTC       384
Leu Leu Leu Gln Ala Ser Ala Glu Val Val Met Glu Gly Gln Pro Leu
        115                 120                 125

TTC CTC AGG TGC CAT GGT TGG AGG AAC TGG GAT GTG TAC AAG GTG ATC       432
Phe Leu Arg Cys His Gly Trp Arg Asn Trp Asp Val Tyr Lys Val Ile
    130                 135                 140

TAT TAT AAG GAT GGT GAA GCT CTC AAG TAC TGG TAT GAG AAC CAC AAC       480
Tyr Tyr Lys Asp Gly Glu Ala Leu Lys Tyr Trp Tyr Glu Asn His Asn
145                 150                 155                 160

ATC TCC ATT ACA AAT GCC ACA GTT GAA GAC AGT GGA ACC TAC TAC TGT       528
Ile Ser Ile Thr Asn Ala Thr Val Glu Asp Ser Gly Thr Tyr Tyr Cys
                165                 170                 175

ACG GGC AAA GTG TGG CAG CTG GAC TAT GAG TCT GAG CCC CTC AAC ATT       576
Thr Gly Lys Val Trp Gln Leu Asp Tyr Glu Ser Glu Pro Leu Asn Ile
            180                 185                 190

ACT GTA ATA AAA GCT CCG CGT GAG AAG TAC TGG CTA CAA TTT TTT ATC       624
Thr Val Ile Lys Ala Pro Arg Glu Lys Tyr Trp Leu Gln Phe Phe Ile
        195                 200                 205

CCA TTG TTG GTG GTG ATT CTG TTT GCT GTG GAC ACA GGA TTA TTT ATC       672
Pro Leu Leu Val Val Ile Leu Phe Ala Val Asp Thr Gly Leu Phe Ile
    210                 215                 220

TCA ACT CAG CAG CAG GTC ACA TTT CTC TTG AAG ATT AAG AGA ACC AGG       720
Ser Thr Gln Gln Gln Val Thr Phe Leu Leu Lys Ile Lys Arg Thr Arg
225                 230                 235                 240

AAA GGC TTC AGA CTT CTG AAC CCA CAT CCT AAG CCA AAC CCC AAA AAC       768
```

Lys Gly Phe Arg Leu Leu Asn Pro His Pro Lys Pro Asn Pro Lys Asn
                245                 250                 255

AAC TGA                                                                774
Asn (2) INFORMATION FOR SEQ ID NO:5:

(i) SEQUENCE CHARACTERISTICS:
        (A) LENGTH: 774 nucleotides
        (B) TYPE: nucleic acid
        (C) STRANDEDNESS: single
        (D) TOPOLOGY: linear (ii) MOLECULE TYPE: cDNA (iii) SEQUENCE DESCRIPTION: SEQ ID NO:5:

```
TCAGTTGTTT TTGGGGTTTG GCTTAGGATG TGGGTTCAGA AGTCTGAAGC CTTTCCTGGT    60
TCTCTTAATC TTCAAGAGAA ATGTGACCTG CTGCTGAGTT GAGATAAATA ATCCTGTGTC   120
CACAGCAAAC AGAATCACCA CCAACAATGG GATAAAAAAT TGTAGCCAGT ACTTCTCACG   180
CGGAGCTTTT ATTACAGTAA TGTTGAGGGG CTCAGACTCA TAGTCCAGCT GCCCACACTTT   240
GCCCGTACAG TAGTAGGTTC CACTGTCTTC AACTGTGGCA TTTGTAATGG AGATGTTGTG   300
GTTCTCATAC CAGTACTTGA GAGCTTCACC ATCCTTATAA TAGATCACCT TGTACACATC   360
CCAGTTCCTC CAACCATGGC ACCTGAGGAA GAGGGGCTGG CCCTCCATCA CCACCTCAGC   420
AGAGGCCTGA AGGAGCAGCC AGTCACTGAA GACTTCCAGG TACACAGGTT CACTCTCATT   480
AACTTGTTGG TGCTGACATT TGTATTCTCC ACTGTCTTCA AATTTGGCAT TCACAATATT   540
CAAACTTGAA TTTGTCTCTT CTGAAAGGCT GCCATTGTGG AACCATTTGG TGGAACTGAC   600
TTCAAAGAAA TTGTTCCCAT TACATGTAAG AGTCACATTC TCTCCTTTAA ATATTCTATT   660
CCATGGAGGG TTCAAGGAGA CCTTAGGTTT CTGAGGGACT GCTAACACGC CATCTGGAGC   720
GAAGAACAGT AAGGCTACAC ACAGTAGAGT AGGGGATTCC ATGGCAGGAG CCAT         774
```

(2) INFORMATION FOR SEQ ID NO:6:

(i) SEQUENCE CHARACTERISTICS:
        (A) LENGTH: 232 amino acids
        (B) TYPE: amino acid
        (D) TOPOLOGY: linear (ii) MOLECULE TYPE: protein (iii) SEQUENCE DESCRIPTION: SEQ ID NO:6:

Val Pro Gln Lys Pro Lys Val Ser Leu Asn Pro Pro Trp Asn Arg Ile
  1               5                  10                  15

Phe Lys Gly Glu Asn Val Thr Leu Thr Cys Asn Gly Asn Asn Phe Phe
                 20                  25                  30

Glu Val Ser Ser Thr Lys Trp Phe His Asn Gly Ser Leu Ser Glu Glu
             35                  40                  45

Thr Asn Ser Ser Leu Asn Ile Val Asn Ala Lys Phe Glu Asp Ser Gly
         50                  55                  60

Glu Tyr Lys Cys Gln His Gln Gln Val Asn Glu Ser Glu Pro Val Tyr
 65                  70                  75                  80

Leu Glu Val Phe Ser Asp Trp Leu Leu Leu Gln Ala Ser Ala Glu Val
                 85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys

```
                       115                  120                      125
Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Phe Phe Ile Pro Leu Leu Val Ile Leu Phe Ala
            180                 185                 190

Val Asp Thr Gly Leu Phe Ile Ser Thr Gln Gln Val Thr Phe Leu
            195                 200                 205

Leu Lys Ile Lys Arg Thr Arg Lys Gly Phe Arg Leu Leu Asn Pro His
    210                 215                 220

Pro Lys Pro Asn Pro Lys Asn Asn
225                 230

(2) INFORMATION FOR SEQ ID NO:7:

(i) SEQUENCE CHARACTERISTICS:
         (A) LENGTH:  699 nucleotides
         (B) TYPE:  nucleic acid
         (C) STRANDEDNESS:  single
         (D) TOPOLOGY:  linear (ii) MOLECULE TYPE:  cDNA (iii) FEATURE:
         (A) NAME/KEY:  CDS
         (B) LOCATION:  1..699

(iii) SEQUENCE DESCRIPTION:  SEQ ID NO:7:

GTC CCT CAG AAA CCT AAG GTC TCC TTG AAC CCT CCA TGG AAT AGA ATA      48
Val Pro Gln Lys Pro Lys Val Ser Leu Asn Pro Pro Trp Asn Arg Ile
  1               5                  10                  15

TTT AAA GGA GAG AAT GTG ACT CTT ACA TGT AAT GGG AAC AAT TTC TTT      96
Phe Lys Gly Glu Asn Val Thr Leu Thr Cys Asn Gly Asn Asn Phe Phe
                 20                  25                  30

GAA GTC AGT TCC ACC AAA TGG TTC CAC AAT GGC AGC CTT TCA GAA GAG     144
Glu Val Ser Ser Thr Lys Trp Phe His Asn Gly Ser Leu Ser Glu Glu
             35                  40                  45

ACA AAT TCA AGT TTG AAT ATT GTG AAT GCC AAA TTT GAA GAC AGT GGA     192
Thr Asn Ser Ser Leu Asn Ile Val Asn Ala Lys Phe Glu Asp Ser Gly
         50                  55                  60

GAA TAC AAA TGT CAG CAC CAA CAA GTT AAT GAG AGT GAA CCT GTG TAC     240
Glu Tyr Lys Cys Gln His Gln Gln Val Asn Glu Ser Glu Pro Val Tyr
 65                  70                  75                  80

CTG GAA GTC TTC AGT GAC TGG CTG CTC CTT CAG GCC TCT GCT GAG GTG     288
Leu Glu Val Phe Ser Asp Trp Leu Leu Leu Gln Ala Ser Ala Glu Val
                 85                  90                  95

GTG ATG GAG GGC CAG CCC CTC TTC CTC AGG TGC CAT GGT TGG AGG AAC     336
Val Met Glu Gly Gln Pro Leu Phe Leu Arg Cys His Gly Trp Arg Asn
            100                 105                 110

TGG GAT GTG TAC AAG GTG ATC TAT TAT AAG GAT GGT GAA GCT CTC AAG     384
Trp Asp Val Tyr Lys Val Ile Tyr Tyr Lys Asp Gly Glu Ala Leu Lys
        115                 120                 125

TAC TGG TAT GAG AAC CAC AAC ATC TCC ATT ACA AAT GCC ACA GTT GAA     432
Tyr Trp Tyr Glu Asn His Asn Ile Ser Ile Thr Asn Ala Thr Val Glu
    130                 135                 140

GAC AGT GGA ACC TAC TAC TGT ACG GGC AAA GTG TGG CAG CTG GAC TAT     480
Asp Ser Gly Thr Tyr Tyr Cys Thr Gly Lys Val Trp Gln Leu Asp Tyr
145                 150                 155                 160
```

```
GAG TCT GAG CCC CTC AAC ATT ACT GTA ATA AAA GCT CCG CGT GAG AAG       528
Glu Ser Glu Pro Leu Asn Ile Thr Val Ile Lys Ala Pro Arg Glu Lys
            165                 170                 175

TAC TGG CTA CAA TTT TTT ATC CCA TTG TTG GTG GTG ATT CTG TTT GCT       576
Tyr Trp Leu Gln Phe Phe Ile Pro Leu Leu Val Val Ile Leu Phe Ala
            180                 185                 190

GTG GAC ACA GGA TTA TTT ATC TCA ACT CAG CAG CAG GTC ACA TTT CTC       624
Val Asp Thr Gly Leu Phe Ile Ser Thr Gln Gln Gln Val Thr Phe Leu
            195                 200                 205

TTG AAG ATT AAG AGA ACC AGG AAA GGC TTC AGA CTT CTG AAC CCA CAT       672
Leu Lys Ile Lys Arg Thr Arg Lys Gly Phe Arg Leu Leu Asn Pro His
    210                 215                 220

CCT AAG CCA AAC CCC AAA AAC AAC TGA                                   699
Pro Lys Pro Asn Pro Lys Asn Asn
225                 230
```

(2) INFORMATION FOR SEQ ID NO:8:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: primer (iii) SEQUENCE DESCRIPTION: SEQ ID NO:8:

```
CGCGGATCCT ATAAATATGG CTCCTGCCAT GG                                    32
```

(2) INFORMATION FOR SEQ ID NO:9:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: primer (iii) SEQUENCE DESCRIPTION: SEQ ID NO:9:
```
GGCGAATTCT TAAGCTTTTA TTACAG                                           26
```

(2) INFORMATION FOR SEQ ID NO:10:

(i) SEQUENCE CHARACTERISTICS:
        (A) LENGTH: 591 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..591

(iv) SEQUENCE DESCRIPTION: SEQ ID NO:10:

```
ATG GCT CCT GCC ATG GAA TCC CCT ACT CTA CTG TGT GTA GCC TTA CTG        48
Met Ala Pro Ala Met Glu Ser Pro Thr Leu Leu Cys Val Ala Leu Leu
 1               5                  10                  15

TTC TTC GCT CCA GAT GGC GTG TTA GCA GTC CCT CAG AAA CCT AAG GTC        96
Phe Phe Ala Pro Asp Gly Val Leu Ala Val Pro Gln Lys Pro Lys Val
                20                  25                  30

TCC TTG AAC CCT CCA TGG AAT AGA ATA TTT AAA GGA GAG AAT GTG ACT       144
Ser Leu Asn Pro Pro Trp Asn Arg Ile Phe Lys Gly Glu Asn Val Thr
            35                  40                  45
```

```
CTT ACA TGT AAT GGG AAC AAT TTC TTT GAA GTC AGT TCC ACC AAA TGG          192
Leu Thr Cys Asn Gly Asn Asn Phe Phe Glu Val Ser Ser Thr Lys Trp
    50                  55                  60

TTC CAC AAT GGC AGC CTT TCA GAA GAG ACA AAT TCA AGT TTG AAT ATT          240
Phe His Asn Gly Ser Leu Ser Glu Glu Thr Asn Ser Ser Leu Asn Ile
65                  70                  75                  80

GTG AAT GCC AAA TTT GAA GAC AGT GGA GAA TAC AAA TGT CAG CAC CAA          288
Val Asn Ala Lys Phe Glu Asp Ser Gly Glu Tyr Lys Cys Gln His Gln
                85                  90                  95

CAA GTT AAT GAG AGT GAA CCT GTG TAC CTG GAA GTC TTC AGT GAC TGG          336
Gln Val Asn Glu Ser Glu Pro Val Tyr Leu Glu Val Phe Ser Asp Trp
            100                 105                 110

CTG CTC CTT CAG GCC TCT GCT GAG GTG GTG ATG GAG GGC CAG CCC CTC          384
Leu Leu Leu Gln Ala Ser Ala Glu Val Val Met Glu Gly Gln Pro Leu
            115                 120                 125

TTC CTC AGG TGC CAT GGT TGG AGG AAC TGG GAT GTG TAC AAG GTG ATC          432
Phe Leu Arg Cys His Gly Trp Arg Asn Trp Asp Val Tyr Lys Val Ile
    130                 135                 140

TAT TAT AAG GAT GGT GAA GCT CTC AAG TAC TGG TAT GAG AAC CAC AAC          480
Tyr Tyr Lys Asp Gly Glu Ala Leu Lys Tyr Trp Tyr Glu Asn His Asn
145                 150                 155                 160

ATC TCC ATT ACA AAT GCC ACA GTT GAA GAC AGT GGA ACC TAC TAC TGT          528
Ile Ser Ile Thr Asn Ala Thr Val Glu Asp Ser Gly Thr Tyr Tyr Cys
                165                 170                 175

ACG GGC AAA GTG TGG CAG CTG GAC TAT GAG TCT GAG CCC CTC AAC ATT          576
Thr Gly Lys Val Trp Gln Leu Asp Tyr Glu Ser Glu Pro Leu Asn Ile
            180                 185                 190

ACT GTA ATA AAA GCT                                                      591
Thr Val Ile Lys Ala
        195
```

(2) INFORMATION FOR SEQ ID NO:11:

(i) SEQUENCE CHARACTERISTICS:
        (A) LENGTH: 197 amino acids
        (B) TYPE: amino acid
        (D) TOPOLOGY: linear (ii) MOLECULE TYPE: protein (iii) SEQUENCE DESCRIPTION: SEQ ID NO:11:

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
            115                 120                 125

Phe Leu Arg Cys His Gly Trp Arg Asn Trp Asp Val Tyr Lys Val Ile
    130                 135                 140
```

```
Tyr Tyr Lys Asp Gly Glu Ala Leu Lys Tyr Trp Tyr Glu Asn His Asn
    145                 150                 155                 160

Ile Ser Ile Thr Asn Ala Thr Val Glu Asp Ser Gly Thr Tyr Tyr Cys
165                 170                 175

Thr Gly Lys Val Trp Gln Leu Asp Tyr Glu Ser Glu Pro Leu Asn Ile
                180                 185                 190

Thr Val Ile Lys Ala
            195
```

(2) INFORMATION FOR SEQ ID NO:12:

(i) SEQUENCE CHARACTERISTICS:
        (A) LENGTH: 516 nucleotides
        (B) TYPE: nucleic acid
        (C) STRANDEDNESS: single
        (D) TOPOLOGY: linear (ii) MOLECULE TYPE: cDNA (iii) FEATURE:
        (A) NAME/KEY: CDS
        (B) LOCATION: 1..516

(xi) SEQUENCE DESCRIPTION: SEQ ID NO:12:

```
GTC CCT CAG AAA CCT AAG GTC TCC TTG AAC CCT CCA TGG AAT AGA ATA    48
Val Pro Gln Lys Pro Lys Val Ser Leu Asn Pro Pro Trp Asn Arg Ile
1               5                   10                  15

TTT AAA GGA GAG AAT GTG ACT CTT ACA TGT AAT GGG AAC AAT TTC TTT    96
Phe Lys Gly Glu Asn Val Thr Leu Thr Cys Asn Gly Asn Asn Phe Phe
                20                  25                  30

GAA GTC AGT TCC ACC AAA TGG TTC CAC AAT GGC AGC CTT TCA GAA GAG   144
Glu Val Ser Ser Thr Lys Trp Phe His Asn Gly Ser Leu Ser Glu Glu
            35                  40                  45

ACA AAT TCA AGT TTG AAT ATT GTG AAT GCC AAA TTT GAA GAC AGT GGA   192
Thr Asn Ser Ser Leu Asn Ile Val Asn Ala Lys Phe Glu Asp Ser Gly
        50                  55                  60

GAA TAC AAA TGT CAG CAC CAA CAA GTT AAT GAG AGT GAA CCT GTG TAC   240
Glu Tyr Lys Cys Gln His Gln Gln Val Asn Glu Ser Glu Pro Val Tyr
65                  70                  75                  80

CTG GAA GTC TTC AGT GAC TGG CTG CTC CTT CAG GCC TCT GCT GAG GTG   288
Leu Glu Val Phe Ser Asp Trp Leu Leu Leu Gln Ala Ser Ala Glu Val
                85                  90                  95

GTG ATG GAG GGC CAG CCC CTC TTC CTC AGG TGC CAT GGT TGG AGG AAC   336
Val Met Glu Gly Gln Pro Leu Phe Leu Arg Cys His Gly Trp Arg Asn
            100                 105                 110

TGG GAT GTG TAC AAG GTG ATC TAT TAT AAG GAT GGT GAA GCT CTC AAG   384
Trp Asp Val Tyr Lys Val Ile Tyr Tyr Lys Asp Gly Glu Ala Leu Lys
        115                 120                 125

TAC TGG TAT GAG AAC CAC AAC ATC TCC ATT ACA AAT GCC ACA GTT GAA   432
Tyr Trp Tyr Glu Asn His Asn Ile Ser Ile Thr Asn Ala Thr Val Glu
130                 135                 140

GAC AGT GGA ACC TAC TAC TGT ACG GGC AAA GTG TGG CAG CTG GAC TAT   480
Asp Ser Gly Thr Tyr Tyr Cys Thr Gly Lys Val Trp Gln Leu Asp Tyr
145                 150                 155                 160

GAG TCT GAG CCC CTC AAC ATT ACT GTA ATA AAA GCT                   516
Glu Ser Glu Pro Leu Asn Ile Thr Val Ile Lys Ala
                165                 170
```

(2) INFORMATION FOR SEQ ID NO:13:

(i) SEQUENCE CHARACTERISTICS:
        (A) LENGTH: 172 amino acids
        (B) TYPE: amino acid -continued

```
        (D) TOPOLOGY:  linear (ii) MOLECULE TYPE:  protein (xi) SEQUENCE DESCRIPTION:  SEQ ID NO:13:

Val Pro Gln Lys Pro Lys Val Ser Leu Asn Pro Pro Trp Asn Arg Ile
 1               5                  10                  15

Phe Lys Gly Glu Asn Val Thr Leu Thr Cys Asn Gly Asn Asn Phe Phe
             20                  25                  30

Glu Val Ser Ser Thr Lys Trp Phe His Asn Gly Ser Leu Ser Glu Glu
             35                  40                  45

Thr Asn Ser Ser Leu Asn Ile Val Asn Ala Lys Phe Glu Asp Ser Gly
             50                  55                  60

Glu Tyr Lys Cys Gln His Gln Gln Val Asn Glu Ser Glu Pro Val Tyr
 65                  70                  75                  80

Leu Glu Val Phe Ser Asp Trp Leu Leu Leu Gln Ala Ser Ala Glu Val
                 85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
            130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala
                165                 170
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to detect flea allergy dermatitis comprising:
   a. immobilizing a flea allergen on a substrate;
   b. contacting said flea allergen with a putative IgE-containing composition under conditions suitable for formation of an antigen:IgE complex bound to said substrate;
   c. removing non-bound material from said substrate under conditions that retain antigen:IgE complex binding to said substrate; and
   d. detecting the presence of said antigen:IgE complex by contacting said antigen:IgE complex with a $Fc_\epsilon R$ molecule and removing non-bound $Fc_\epsilon R$ molecule under conditions that retain bound $Fc_\epsilon R$ molecule, the presence of said $Fc_\epsilon R$ molecule indicating the presence of said IgE:antigen complex.

2. The method of claim 1, wherein said flea allergen is a flea saliva antigen.

3. The method of claim 1, wherein said flea allergen is selected from the group consisting of flea saliva products and flea saliva proteins.

4. The method of claim 1, wherein said putative IgE-containing composition comprises an animal fluid selected from the group consisting of serum, plasma and blood.

5. The method of claim 4, wherein said animal is selected from the group consisting of a dog and a cat.

6. The method of claim 1, wherein said $Fc_\epsilon R$ molecule comprises at least a portion of a $Fc_\epsilon R$ alpha chain that binds to IgE.

7. A kit for detecting flea allergy dermatitis comprising a human $Fc_\epsilon$ receptor ($Fc_\epsilon R$) molecule and at least one flea allergen.

8. The kit of claim 7, wherein said at least one flea allergen is selected from the group consisting of a flea saliva product and a flea saliva protein.

9. The kit of claim 7, wherein said at least one flea allergen comprises flea saliva products.

10. The kit of claim 7, wherein said human $Fc_\epsilon R$ molecule is conjugated to a detectable marker.

11. The kit of claim 7, wherein said human $Fc_\epsilon R$ molecule is conjugated to biotin.

12. The kit of claim 7, wherein said human $Fc_\epsilon R$ molecule comprises at least a portion of a $Fc_\epsilon R$ alpha chain that binds to IgE.

13. The method of claim 1, wherein said putative IgE-containing composition comprises a composition selected from the group consisting of blood, serum, plasma, urine, tears, aqueous humor, central nervous system fluid (CNF), saliva, lymph, nasal secretions, milk and feces.

14. The method of claim 1, wherein said $Fc_\epsilon R$ molecule is conjugated to a detectable marker.

15. The method of claim 1, wherein said step of detecting comprises performing assays selected from the group consisting of enzyme-linked immunoassays, radioimmunoassays, immunoprecipitations, fluorescence immunoassays, chemiluminescent assay, immunoblot assays, lateral flow assays, agglutination assays and particulate-based assays.

16. The kit of claim 7, wherein a component selected from the group consisting of said human $Fc_\epsilon$ receptor and said at least one flea allergen is immobilized on a substrate.

17. The kit of claim 16, wherein said substrate comprises a shape selected from the group consisting of a well, a plate, a dipstick, a bead, a lateral flow apparatus, a membrane, a filter, a tube, a dish, a celluloid-type matrix and a magnetic particle.

18. The kit of claim 7 further comprising an apparatus comprising:
   a. a support structure defining a flow path;
   b. a labeling reagent comprising a bead conjugated to said at least one flea allergen, wherein said labeling reagent is impregnated within the support structure in a labeling zone; and
   c. a capture reagent comprising said $Fc_\epsilon R$ molecule, wherein said capture reagent is located downstream of said labeling reagent within a capture zone fluidly connected to said labeling zone in such a manner that said labeling reagent can flow from said labeling zone into said capture zone.

19. The kit of claim 12, wherein a carbohydrate group of said human $Fc_\epsilon R$ alpha chain is conjugated to biotin.

20. A method for the detection of flea allergy dermatitis comprising:
   a. immobilizing on a substrate an $Fc_\epsilon R$ molecule;
   b. contacting said substrate with a putative IgE-containing composition under conditions suitable for formation of complex formation between said IgE and said $Fc_\epsilon R$ molecule, to form an IgE-containing complex; and
   c. detecting the presence of said IgE-containing complex by contacting said complex with at least one flea allergen and removing non-bound allergen under conditions that retain bound allergen, the presence of said flea allergen indicating the presence of said IgE-containing complex.

* * * * *